United States Patent
Hubbell

(10) Patent No.: US 10,619,205 B2
(45) Date of Patent: Apr. 14, 2020

(54) COMBINATORIAL BARCODE SEQUENCES, AND RELATED SYSTEMS AND METHODS

(71) Applicant: LIFE TECHNOLOGIES CORPORATION, Carlsbad, CA (US)

(72) Inventor: Earl Hubbell, Palo Alto, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 39 days.

(21) Appl. No.: 15/588,203

(22) Filed: May 5, 2017

(65) Prior Publication Data

US 2017/0321271 A1    Nov. 9, 2017

Related U.S. Application Data

(60) Provisional application No. 62/401,632, filed on Sep. 29, 2016, provisional application No. 62/332,862, filed on May 6, 2016.

(51) Int. Cl.
| | | |
|---|---|---|
| C12Q 1/68 | (2018.01) |
| B01J 19/00 | (2006.01) |
| C12N 15/10 | (2006.01) |
| C12Q 1/6874 | (2018.01) |
| C40B 20/04 | (2006.01) |
| C40B 70/00 | (2006.01) |

(52) U.S. Cl.
CPC ........ *C12Q 1/6874* (2013.01); *B01J 19/0046* (2013.01); *C12N 15/1065* (2013.01); *C40B 20/04* (2013.01); *C40B 70/00* (2013.01); *B01J 2219/00547* (2013.01); *B01J 2219/00572* (2013.01); *B01J 2219/00722* (2013.01)

(58) Field of Classification Search
None
See application file for complete search history.

(56) References Cited

U.S. PATENT DOCUMENTS

| | | |
|---|---|---|
| 2,632,058 A | 3/1953 | Frank et al. |
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,210,015 A | 5/1993 | Gelfand et al. |
| 5,399,491 A | 3/1995 | Kacian et al. |
| 5,750,341 A | 5/1998 | Macevicz |
| 5,854,033 A | 12/1998 | Lizardi |
| 6,172,214 B1 | 1/2001 | Brenner |
| 6,174,670 B1 | 1/2001 | Wittwer et al. |
| 6,210,891 B1 | 4/2001 | Nyren et al. |
| 6,235,475 B1 | 5/2001 | Brenner et al. |
| 6,251,639 B1 | 6/2001 | Kurn |
| 6,258,568 B1 | 7/2001 | Nyren |
| 6,274,320 B1 | 8/2001 | Rothberg et al. |
| 6,404,907 B1 | 6/2002 | Gilchrist et al. |
| 6,780,591 B2 | 8/2004 | Williams et al. |
| 6,828,100 B1 | 12/2004 | Ronaghi |
| 6,833,246 B2 | 12/2004 | Balasubramanian |
| 6,911,327 B2 | 6/2005 | McMillan et al. |
| 7,037,687 B2 | 5/2006 | Williams et al. |
| 7,049,645 B2 | 5/2006 | Sawada et al. |
| 7,117,095 B2 | 10/2006 | Hubbell |
| 7,133,782 B2 | 11/2006 | Odedra |
| 7,211,390 B2 | 5/2007 | Rothberg et al. |
| 7,244,559 B2 | 7/2007 | Rothberg et al. |
| 7,264,929 B2 | 9/2007 | Rothberg et al. |
| 7,323,305 B2 | 1/2008 | Leamon et al. |
| 7,323,309 B2 | 1/2008 | Mirkin et al. |
| 7,335,762 B2 | 2/2008 | Rothberg et al. |
| 7,348,181 B2 | 3/2008 | Walt et al. |
| 7,424,371 B2 | 9/2008 | Kamentsky |
| 7,535,232 B2 | 5/2009 | Barbaro et al. |
| 7,575,865 B2 | 8/2009 | Leamon et al. |
| 7,645,596 B2 | 1/2010 | Williams et al. |
| 7,695,907 B2 | 4/2010 | Miyahara et al. |
| 7,782,237 B2 | 8/2010 | Ronaghi et al. |
| 7,785,862 B2 | 8/2010 | Kim et al. |
| 7,835,871 B2 | 11/2010 | Kain et al. |
| 7,838,226 B2 | 11/2010 | Kamahori et al. |
| 7,867,703 B2 | 1/2011 | Sampson et al. |

(Continued)

FOREIGN PATENT DOCUMENTS

| | | |
|---|---|---|
| EP | 2053132 A1 | 4/2009 |
| GB | 2461127 B | 7/2010 |

(Continued)

OTHER PUBLICATIONS

Ronaghi et al., "A Sequencing Method Based on Real-Time Pyrophosphate", Science, vol. 281:363-365, Jul. 17, 1998.
Margulies et al., "Genome sequencing in microfabricated high-density picolitre reactors", Nature, vol. 437:376-380, Sep. 15, 2005.
Ahmadian et al., "Pyrosequencing: history, biochemistry and future," Clin. Chim. Acta, 363:83-94 (2006).
Aksyonov et al., "Multiplexed DNA sequencing-by-synthesis," Anal. Biochem., 348:127-138 (2006).
Anderson et al., "A System for Multiplexed Direct Electrical Detection of DNA Synthesis," Sens. Actuators B Chem., 129(1):79-86 (2008).
Ashlock et al., "DNA error correcting codes: No crossover," IEEE Symposium on Computational Intelligence in Bioinformatics and Computational Biology, 38-45 (2009).

(Continued)

Primary Examiner — Tracy Vivlemore
Assistant Examiner — Sahana S Kaup
(74) Attorney, Agent, or Firm — Jones Robb, PLLC

(57) ABSTRACT

A kit for use with a nucleic acid sequencing instrument can include a plurality of combinatorial barcodes sequences meeting the following criteria: each of the combinatorial barcode sequences comprise a plurality of iterations of a sequence motif, where the sequence motif comprises a first nucleotide base from a first group of nucleotide bases followed by a second nucleotide base from a second group of nucleotide bases, the first group and the second group differing from each other; and the plurality of combinatorial barcode sequences is at least 1,000,000 different barcode sequences.

20 Claims, 14 Drawing Sheets

Specification includes a Sequence Listing.

(56) References Cited

U.S. PATENT DOCUMENTS

| | | | |
|---|---|---|---|
| 7,875,440 B2 | 1/2011 | Williams et al. |
| 7,888,013 B2 | 2/2011 | Miyahara et al. |
| 7,948,015 B2 | 5/2011 | Rothberg et al. |
| 8,058,055 B2 | 11/2011 | Barrett et al. |
| 8,202,691 B2 | 6/2012 | Steemers et al. |
| 8,262,900 B2 | 9/2012 | Rothberg et al. |
| 8,306,757 B2 | 11/2012 | Rothberg et al. |
| 8,309,307 B2 | 11/2012 | Barrett et al. |
| 8,568,979 B2 | 10/2013 | Stuelpnagel et al. |
| 8,673,627 B2 | 3/2014 | Nobile et al. |
| 2003/0219797 A1 | 11/2003 | Zhao et al. |
| 2003/0232348 A1 | 12/2003 | Jones et al. |
| 2004/0018506 A1 | 1/2004 | Koehler et al. |
| 2004/0197793 A1 | 10/2004 | Hassibi et al. |
| 2004/0197845 A1 | 10/2004 | Hassibi et al. |
| 2005/0084851 A1 | 4/2005 | Ronaghi et al. |
| 2006/0147935 A1 | 7/2006 | Linnarsson |
| 2006/0147983 A1 | 7/2006 | Ouchi |
| 2007/0059733 A1 | 3/2007 | Sundararajan et al. |
| 2007/0059741 A1 | 3/2007 | Kamahori et al. |
| 2007/0092872 A1 | 4/2007 | Rothberg et al. |
| 2007/0207471 A1 | 9/2007 | Osaka et al. |
| 2007/0219367 A1 | 9/2007 | Shchepinov et al. |
| 2007/0281300 A1 | 12/2007 | Russell et al. |
| 2008/0166727 A1 | 7/2008 | Esfandyarpour et al. |
| 2008/0182757 A1 | 7/2008 | Heiner et al. |
| 2008/0274904 A1 | 11/2008 | Gormley et al. |
| 2008/0286762 A1 | 11/2008 | Miyahara et al. |
| 2008/0286767 A1 | 11/2008 | Miyahara et al. |
| 2009/0024331 A1 | 1/2009 | Tomaney et al. |
| 2009/0026082 A1 | 1/2009 | Rothberg et al. |
| 2009/0053724 A1 | 2/2009 | Roth et al. |
| 2009/0105959 A1 | 4/2009 | Braverman et al. |
| 2009/0127589 A1 | 5/2009 | Rothberg et al. |
| 2009/0137404 A1 | 5/2009 | Drmanac et al. |
| 2009/0176200 A1 | 7/2009 | Wakita et al. |
| 2009/0221438 A1 | 9/2009 | Kitzman et al. |
| 2009/0312188 A1 | 12/2009 | Duer et al. |
| 2010/0029498 A1 | 2/2010 | Gnirke et al. |
| 2010/0035252 A1 | 2/2010 | Rothberg et al. |
| 2010/0088255 A1 | 4/2010 | Mann |
| 2010/0105052 A1 | 4/2010 | Drmanac et al. |
| 2010/0137143 A1 | 6/2010 | Rothberg et al. |
| 2010/0160172 A1 | 6/2010 | Erlich et al. |
| 2010/0173303 A1 | 7/2010 | Ronaghi et al. |
| 2010/0188073 A1 | 7/2010 | Rothberg et al. |
| 2010/0192032 A1 | 7/2010 | Chen et al. |
| 2010/0197507 A1 | 8/2010 | Rothberg et al. |
| 2010/0199155 A1 | 8/2010 | Kermani et al. |
| 2010/0209922 A1 | 8/2010 | Williams et al. |
| 2010/0267043 A1 | 10/2010 | Braverman et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304447 A1 | 12/2010 | Harris |
| 2010/0323348 A1 | 12/2010 | Hamady et al. |
| 2010/0323350 A1 | 12/2010 | Gordon et al. |
| 2011/0065604 A1 | 3/2011 | Sampson et al. |
| 2011/0160078 A1 | 6/2011 | Fodor et al. |
| 2011/0213563 A1 | 9/2011 | Chen et al. |
| 2011/0230358 A1 | 9/2011 | Rava |
| 2011/0246084 A1 | 10/2011 | Ronaghi et al. |
| 2011/0257889 A1 | 10/2011 | Klammer et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0294115 A1 | 12/2011 | Williams et al. |
| 2012/0035062 A1* | 2/2012 | Schultz ............ C12Q 1/6874 |
| | | 506/7 |
| 2012/0037961 A1 | 2/2012 | Rothberg et al. |
| 2012/0040844 A1 | 2/2012 | Rothberg et al. |
| 2012/0046175 A1 | 2/2012 | Rodesch et al. |
| 2012/0109598 A1 | 5/2012 | Davey et al. |
| 2012/0172241 A1 | 7/2012 | Rearick et al. |
| 2012/0173158 A1 | 7/2012 | Hubbell |
| 2012/0173159 A1 | 7/2012 | Davey et al. |
| 2012/0220494 A1* | 8/2012 | Samuels ............ C12N 15/1075 |
| | | 506/16 |
| 2012/0264621 A1 | 10/2012 | Hubbell et al. |
| 2012/0301926 A1 | 11/2012 | Chen et al. |
| 2013/0053256 A1* | 2/2013 | Hubbell ............ C40B 20/04 |
| | | 506/4 |
| 2013/0060482 A1 | 3/2013 | Sikora et al. |
| 2014/0243232 A1 | 8/2014 | Meredith et al. |
| 2015/0087537 A1 | 3/2015 | Hubbell |
| 2016/0333402 A1 | 11/2016 | Koller et al. |

FOREIGN PATENT DOCUMENTS

| | | |
|---|---|---|
| WO | 2001/001015 A1 | 1/2001 |
| WO | 2005/040425 A2 | 5/2005 |
| WO | 2006084131 A2 | 8/2006 |
| WO | 2008/076406 A2 | 6/2008 |
| WO | 2009/158006 A2 | 12/2009 |
| WO | 2010003153 A2 | 1/2010 |
| WO | 2010/047804 A1 | 4/2010 |
| WO | 2010051978 A1 | 5/2010 |
| WO | 2010/077859 A2 | 7/2010 |
| WO | 2010/117804 A2 | 10/2010 |
| WO | 2010122506 A2 | 10/2010 |
| WO | 2010/138182 A2 | 12/2010 |
| WO | 2012/044847 A1 | 4/2012 |
| WO | 2012129363 A2 | 9/2012 |
| WO | 2013010062 A2 | 1/2013 |

OTHER PUBLICATIONS

Baicheva, "Binary and ternary linear codes which are good and proper for error correction," Institute of Mathematics and Informatics, Bulgarian Academy of Sciences, pp. 1-6, available at http://www.moi.math.bas.bg/~tsonka/ACCT.pdf (last visited Oct. 22, 2013).

Bashiardes, et al., "Direct genomic selection", Nature Methods, vol. 2 No. 1, Jan. 2005, 63-69.

Berger et al., "Compact, universal DNA microarrays to comprehensively determine transcription-factor binding site specificities," Nat. Biotechnol., 24(11):1429-1435 (2006).

P. Bergveld: "Thirty years of ISFETOLOGY: what happened in the past 30 years and what may happen in the next 30 years", Sens. Actuators, vol. 88, 2003, pp. 1-20.

Birren et al.: "Go Analysis: A Laboratory Manual Series", vol. I-IV.

Brenner et al., "Encoded combinatorial chemistry," Proc. Natl. Acad. Sci. USA, 89:5381-5383 (1992).

Breslauer et al., Proceedings National Academy of Science USA, vol. 83, No. 11, 1986, pp. 3746-3750.

Brockman et al., "Quality scores and SNP detection in sequencing-by-synthesis systems," Genome Res., 18:763-770 (2008).

Tilo Buschmann et al., "Levenshtein error-correcting barcodes for multiplexed DNA sequencing", BMC Bioinformatics, vol. 14, No. 1, Jan. 1, 2013.

Leonid V. Bystrykh et al., "Generalized DNA Barcode Design Based on Hamming Codes", vol. 7, No. 5, May 17, 2012.

Casey; Davidson, Nucleic Acids Research, vol. 4, 1977, pp. 1539.

Final Office Action in U.S. Appl. No. 14/505,636, dated Sep. 28, 2015, 16 pages.

Database Geneseq, "HIV1_8 DNA amplicon flanking adaptor, SEQ ID 371", Database accession No. AYL45091 (Dec. 23, 2010).

Dawson et al., "Synthesis of proteins by native chemical ligation", Science, 266:776-779 (1994).

Droege et al., "The Genome Sequencer FLXTM System—Longer reads, more applications, straight forward bioinformatics and more complete data sets," J. Biotechnol., 136:3-10 (2008).

Eltoukhy et al., "Modeling and Base-Calling for DNA Sequencing-By-Synthesis," 2006 IEEE International Conference on Acoustics, Speech, and Signal Processing, II:1032-1035 (2006).

Faircloth et al., "Large sets of edit-metric sequence identification tags to facilitate large-scale multiplexing of reads from massively parallel sequencing," Nature Precedings, 1-15 (2011).

(56) References Cited

OTHER PUBLICATIONS

Fakhrai-Rad et al., "PyrosequencingTM: An Accurate Detection Platform for Single Nucleotide Polymorphisms," Hum. Mutat., 19:479-485 (2002).
Forney, et al., "The Nordstrom-Robinson Code is the Binary Image of the Octacode", Feb. 8, 2001, 11 pages.
Fu et al., "Counting individual DNA molecules by the stochastic attachment of diverse labels," Proc. Natl. Adac. Sci. U.S.A., 108(22):9026-9031 (2011).
Golay, M., "Notes on Digital Coding," Proc. IRE, 37(6):657 (1949).
Gharizadeh, B., "Method Development and Applications of Pyrosequencing Technology," Doctoral Dissertation, Royal Institute of Technology, Stockholm, Sweden (2003).
Gnirke, et al., "Solution hybrid selection with ultra-long oligonucleotides for massively parallel targeted sequencing", Nature Biotechnology, vol. 27 No. 2, Feb. 2009, 182-189.
Hamady et al., "Error-correcting barcoded primers for pyrosequencing hundreds of samples in multiplex," Nat. Methods., 5(3):235-237 (2008).
Hamming, R.W., "Error Detecting and Error Correcting Codes," Bell Syst. Tech. J., 29(2):147-160 (1950) (available at http://www.alcatel-lucent.com/bstj/vol29-1950/articles/bstj29-2-147.pdf).
Hawkins, Nucleic Acids Research, vol. 23, 1995, pp. 22.
Hodges, et al., "Hybrid selection of discrete genomic intervals on custom-designed microarrays for massively parallel sequencing", Nature Protocols, vol. 4 No. 6, 2009, 960-974.
Hoffman, et al., "Coding Theory: The Essentials", Pure and Applied Mathematics, Dec. 1991.
Hytonen et al., BMC Structural Biology, vol. 7, pp. 8.
International Search Report and Written Opinion for International Application No. PCT/US2012/046624, dated Jan. 4, 2013, 15 pages.
International Search Report and Written Opinion for International Application No. PCT/US2016/032442, dated Aug. 5, 2016, 15 pages.
Ji et al., "BM-BC: A Bayesian method of base calling for Solexa sequence data," Department of Biostatistics, The University of Texas M. D. Anderson Cancer Center, Houston, Texas, U.S.A. (http://odin.mdacc.tmc.edu/~ylji/BMBC/bmbc-ie2.pdf), pp. 1-27 (2010).
Kanemasu, M., "Golay Codes," MIT Undergraduate Journal of Mathematics, 1:95-99 (1999) (available at http://www-math.mit.edu/phase2/UJM/vol1/MKANEM~1.PDF).
Krishnan et al., "Barcodes for DNA sequencing with guaranteed error correction capability," Electron. Lett., 47(4):1-2 (2011).
Lee, et al., "Improving the efficiency of genomic loci capture using oligonucleotide arrays for high throughput resequencing", BMC Genomics 2009, 10:646, 12 pages.
Lee, "Some Properties of Nonbinary Error-Correcting Codes," IRE Transactions on Information Theory, 77-82 (1958).
Lehninger: "Biochemistry", 1975, Worth Publishers.
Lennon, N.J., A scalable, fully automated process for construction of sequence-ready barcoded libraries for 454. Genome Biology 11, (2010).
Lin, et al., "Error Control Coding: Fundamentals and Applications", Prentice Hall, Inc., 1983.

Mamanova, et al., "Target-enrichment strategies for next-generation sequencing", Nature Methods, vol. 7 No. 2, Feb. 2010, 111-118.
Margulies et al., Supplementary Methods for the article "Genome sequencing in microfabricated high-density picolitre reactors," Nature, 437:376-380 (2005), pp. 1-34.
Muir, T., "Semisynthesis of proteins by expressed protein ligation," Ann. Rev. Biochem., 72:249-289 (2003).
Muralidharan et al., "Protein ligation: an enabling technology for the biophysical analysis of proteins," Nat. Methods, 3:429-438 (2006).
Page Pacific Biosciences et al: "PacBio SampleNet—Shared Protocol Guidelines for Using PacBio Barcodes for SMRT", Jan. 1, 2014.
Paulus, H., "Protein splicing and related forms of protein autoprocessing", Annu Rev Biochem, 69:447-496 (2000).
Parameswaran, P. et al., A pyrosequencing-tailored nucleotide barcode design unveils opportunities for large-scale sample multiplexing. Nucleic Acids Research 35, e130:1-9 (2007).
PCR Primer: A Laboratory Manual, 2003, Cold Spring Harbor Laboratory Press.
Pourmand et al., "Direct electrical detection of DNA synthesis," Proc. Natl. Adac. Sci. U.S.A., 103(17):6466-6470 (2006).
Pourmand et al., "Multiplex Pyrosequencing," Nucleic Acids Res., 30(7)(e31):1-5 (2002).
Purushothaman, et al., "Towards Fast Solid State DNA Sequencing", IEEE ISCAS 2002 Proceedings, IV-169-IV-172.
Qiu et al., "DNA Sequence-Based "Bar Codes" for Tracking the Origins of Expressed Sequence Tags from a Maize cDNA Library Constructed Using Multiple mRNA Sources," Plant Physiol., 133:475-481 (2003).
Ronaghi, "Pyrosequencing Sheds Light on DNA Sequencing," Genome Res., 11:3-11 (2001).
Rychlik et al., Nucleic Acids Research, vol. 18, No. 21, 1990, pp. 6409-6412.
Sakata, et al., "DBA Sequencing Based on Intrinsic Molecular Charges", Angewandte Chemie 2006, 118, 2283-2286.
Sakurai, et al., "Real-Time Monitoring of DNA Polymerase Reactions by a Micro ISFET pH Sensor", Anal. Chem. 1992, 64, 1996-1997.
Schwartz et al., "The Structure of Single-Track Gray Codes," IEEE Transactions on Information Theory, 45(7):2383-2396 (1999).
Shiroguchi et al., "Digital RNA sequencing minimizes sequence-dependent bias and amplification noise with optimized single-molecule barcodes," Proc. Natl. Adac. Sci. U.S.A., 109(4):1347-1352 (2012).
Tewhey et al., "Enrichment of sequencing targets from the human genome by solution hybridization," Genome Biology 2009, 10:R116.
Yan et al., "Yeast Barcoders: a chemogenomic application of a universal donor-strain collection carrying bar-code identifiers," Nat. Methods, 5(8):719-725 (2008).
Wetmur, Critical Reviews in Biochemistry and Molecular Biology, vol. 26, 1991, pp. 227-259.
Wetmur, J. Mol. Biol., vol. 31, 1966, pp. 349-370.

* cited by examiner

SEQUENCE LISTING

<160> NUMBER OF SEQ ID NOS: 8

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
hvkhvkhvkh vkhvk                                                      15

<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tttttctttc ttct                                                       14

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tactacgacg tcgtagtac                                                  19

<210> SEQ ID NO 4
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gtagtagtac g                                                          11

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gggttaggta aagtttacg                                                  19

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtagtactac gacgtcgt                                                   18

```
<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
hvkhvkhvkm bdmbdmbd                                                    18

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, t, g, unknown or other
<220> FEATURE:
<221> NAME/KEY: modified_base
<222> LOCATION: (7)..(9)
<223> OTHER INFORMATION: a, c, t, g, unknown or other

<400> SEQUENCE: 8
nnnactnnnt ga                                                          12
```

COMBINATORIAL BARCODE SEQUENCES, AND RELATED SYSTEMS AND METHODS

PRIORITY

This application claims the benefit of U.S. Prov. Pat. Appl. No. 62/401,632, filed Sep. 29, 2016, and U.S. Prov. Pat. Appl. No. 62/332,862, filed May 6, 2016, both of which are incorporated by reference herein in entirety.

SEQUENCE LISTING

The instant application contains a Sequence Listing which has been submitted electronically in ASCII format and is hereby incorporated by reference in its entirety. Said ASCII copy, created on Jul. 21, 2017, is named LT01153US_SL.txt and is 2,375 bytes in size.

FIELD

The present disclosure generally relates to methods, systems, kits, and devices for sample identification, and, more specifically, to methods, systems, kits, and devices for designing, and/or making, and/or using sample discriminating codes or barcodes for identifying sample nucleic acids or other biomolecules or polymers.

INTRODUCTION

Various instruments, apparatuses, and/or systems perform sequencing of nucleic acid sequences using sequencing-by-synthesis, including, for example, the Genome Analyzer/HiSeq/MiSeq platforms (Illumina, Inc.; see, e.g., U.S. Pat. Nos. 6,833,246 and 5,750,341); the GS FLX, GS FLX Titanium, and GS Junior platforms (Roche/454 Life Sciences; see, e.g., Ronaghi et al., SCIENCE, 281:363-365 (1998), and Margulies et al., NATURE, 437:376-380 (2005)); and the Ion PGM™ and Ion Proton™ Sequencers (Life Technologies Corp./Ion Torrent; see, e.g., U.S. Pat. No. 7,948,015 and U.S. Pat. Appl. Publ. Nos. 2010/0137143, 2009/0026082, and 2010/0282617), which are all incorporated by reference herein in their entirety. In order to increase sequencing throughput and/or lower costs for sequencing-by-synthesis (and other sequencing methods such as, e.g., sequencing-by-hybridization, sequencing-by-ligation, etc.), there is a need for new methods, systems, computer readable media, and kits that allow highly efficient preparation and/or identification of samples of potentially high complexity.

SUMMARY

The present disclosure generally relates to methods, systems, kits, and devices for sample identification, and, more specifically, to methods, systems, and kits for designing, and/or making, and/or using sample discriminating codes or barcodes for identifying sample nucleic acids or other biomolecules or polymers.

In accordance with an exemplary embodiment of the present disclosure, a kit for use with a nucleic acid sequencing instrument can include a plurality of combinatorial barcodes sequences meeting the following criteria: each of the combinatorial barcode sequences comprise a plurality of iterations of a sequence motif, where the sequence motif comprises a first nucleotide base from a first group of nucleotide bases followed by a second nucleotide base from a second group of nucleotide bases, the first group and the second group differing from each other; and the plurality of combinatorial barcode sequences is at least 1,000,000 different barcode sequences.

In some embodiments, the first group comprises at least two nucleotide bases and the second group comprises at least two nucleotide bases. In some embodiments, the plurality of combinatorial barcodes sequences have a length comprising a length for the sequence motif multiplied by a number of iterations for the sequence motif. In some embodiments, the plurality of combinatorial barcodes sequences are synchronized in flow space when associated with a predetermined order of nucleotide flows based on the sequence motif.

In accordance with an exemplary embodiment of the present disclosure, a method for nucleic acid sequencing is disclosed. A combinatorial barcode sequence may be incorporated into a polynucleotide to create a tagged polynucleotide, the combinatorial barcode sequence comprising at least two iterations of a sequence motif, wherein the sequence motif comprises a first nucleotide base from a first group of nucleotide bases followed by a second nucleotide base from a second group of nucleotide bases, the first group and the second group differing from each other. Reactions to the tagged polynucleotide may be caused by introducing sequential nucleotide flows comprising one species of nucleotide, the flows being in a predetermined order based on the nucleotide species, wherein the reacting comprises incorporations of nucleotides from the nucleotide flows into the tagged polynucleotide over the barcode sequence. A series of signals over the barcode sequence resulting from the incorporations may be detected, wherein the predetermined order of nucleotide flows comprises a repetition of a flow order motif that is based on the sequence motif. The detected series of signals may be resolved to determine the combinatorial barcode sequence.

In some embodiments, the predetermined order of nucleotide flows comprises a modified portion of a first flow order for sequencing the tagged polynucleotide. In some embodiments, the first group comprises at least two nucleotide bases and the second group comprises at least two nucleotide bases. In some embodiments, the sequence motif further comprises, following the second nucleotide base, a third nucleotide base from a third group of nucleotide bases followed by a fourth nucleotide base from a fourth group of nucleotide bases, the third group comprising at least two nucleotide bases and the fourth group comprising at least two nucleotide bases, each of the first, second, third and fourth groups differing from each other. In some embodiments, the sequence motif comprises 16 possible combinations of nucleotide bases. In some embodiments, a length of the combinatorial barcode sequence is 20 nucleotide bases that correspond to 5 iterations of the sequence motif or 24 nucleotide bases that correspond to 6 iterations of the sequence motif. In some embodiments, the combinatorial barcode is one of over 1,000,000 potential combinatorial barcode sequences based on 5 iterations of the sequence motif.

In some embodiments, the first group comprises at least three nucleotide bases and the second group comprises at least three nucleotide bases. In some embodiments, the sequence motif further comprises, following the second nucleotide base, a third nucleotide base from a third group of nucleotide bases, the third group comprising at least two nucleotide bases, each of the first, second, and third groups differing from each other. In some embodiments, the sequence motif comprises 18 possible combinations of nucleotide bases. In some embodiments, a length for the combinatorial barcode sequence is 15 nucleotide bases that correspond to 5 iterations of the sequence motif or 18 nucleotide bases that correspond to 6 iterations of the sequence motif. In some embodiments, the combinatorial barcode is one of over 1,000,000 potential combinatorial barcode sequences based on 5 iterations of the sequence motif.

In some embodiments, the combinatorial barcodes sequence has a length comprising a length for the sequence motif multiplied by a number of iterations for the sequence motif. In some embodiments, the combinatorial barcode sequence is one of over 1,000,000 potential combinatorial barcode sequences based on a plurality of iterations for the sequencing motif. In some embodiments, the potential combinatorial barcode sequences are synchronized in flow space based on the predetermined order of nucleotide flows.

In accordance with an exemplary embodiment of the present disclosure, a system for nucleic acid sequencing is disclosed. The system comprises a sequencing device configured to introduce sequential nucleotide flows comprising one species of nucleotide to a tagged polynucleotide comprising a combinatorial barcode sequence, the flows being in a predetermined order based on the nucleotide species, wherein the combinatorial barcode sequence comprises at least two iterations of a sequence motif, the sequence motif comprising at least a first nucleotide base from a first group of nucleotide bases followed by a second nucleotide base from a second group of nucleotide bases, first group and the second group differing from each other, and the introducing causes incorporations of nucleotides from the nucleotide flows into the tagged polynucleotide over the barcode sequence. The sequencing device is also configured to detect a series of signals over the barcode sequence resulting from the incorporations, wherein the predetermined order of nucleotide flows comprises a repetition of a flow order motif that is based on the sequence motif. The system also comprises a computing device configured to resolve the detected series of signals to determine the combinatorial barcode sequence.

BRIEF DESCRIPTION OF THE DRAWINGS

The accompanying drawings, which are incorporated into and form a part of the specification, illustrate one or more exemplary embodiments and serve to explain the principles of various exemplary embodiments. The drawings are exemplary and explanatory only and are not to be construed as limiting or restrictive in any way.

DETAILED DESCRIPTION

Figure 1:
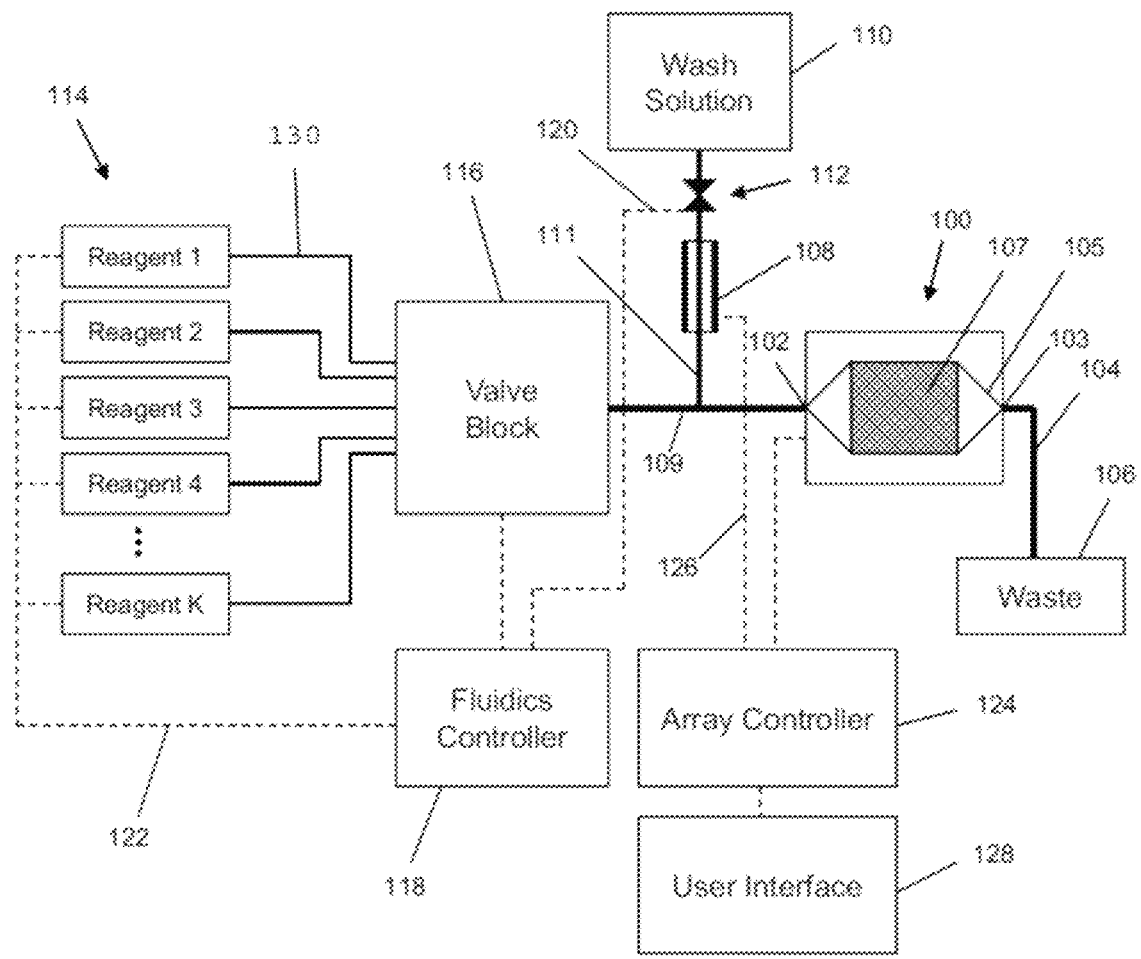
FIG. 1 is a block diagram illustrating components of an exemplary system for nucleic acid sequencing.

The following description and the various embodiments described herein are exemplary and explanatory only and are not to be construed as limiting or restrictive in any way. Other embodiments, features, objects, and advantages of the present teachings will be apparent from the description and accompanying drawings, and from the claims.

Various exemplary embodiments of the present disclosure permit efficient preparation and/or identification of biological samples. In some exemplary embodiments, combinatorial barcode sequences are used to increase manufacturing and sequencing efficiency. For example, the predetermined pattern of bases for a combinatorial barcode sequence can allow for efficient manufacturing. In addition, the predetermined pattern can be coordinate along with a flow order when sequencing to provide further improvements to sequencing technology, such as flow synchronization techniques and out of phase and PCR amplification error mitigation techniques.

Some embodiments may acheive identification of an origin of samples used in sequencing. Such identification may involve an analysis of sequencing data for the samples. The source of the sequencing data may be uniquely tagged, coded, or identified (e.g., to resolve a particular nucleic acid species associated with a particular sample population). Such identification may be facilitated by using sample discriminating codes or sequences (also known as barcodes, e.g., synthetic nucleic acid barcodes) that may be embedded within or otherwise associated with the samples. Various disclosed embodiments also can generate a large number of potential barcodes that may be used to discriminate samples, for instance from one another.

Unless otherwise specifically designated herein, terms, techniques, and symbols of biochemistry, cell biology, cell and tissue culture, genetics, molecular biology, nucleic acid chemistry, and organic chemistry (including chemical and physical analysis of polymer particles, enzymatic reactions and purification, nucleic acid purification and preparation, nucleic acid sequencing and analysis, polymerization techniques, preparation of synthetic polynucleotides, recombinant techniques, etc.) used herein follow those of standard treatises and texts in the relevant field. See, e.g., Kornberg and Baker, DNA REPLICATION, 2nd ed. (W. H. Freeman, New York, 1992); Lehninger, BIOCHEMISTRY, 2nd ed. (Worth Publishers, New York, 1975); Strachan and Read, HUMAN MOLECULAR GENETICS, 2nd ed. (Wiley-Liss, New York, 1999); Birren et al. (eds.), GENOME ANALYSIS: A LABORATORY MANUAL SERIES (Vols. I-IV), Dieffenbach and Dveksler (eds.), PCR PRIMER: A LABORATORY MANUAL, and Green and Sambrook (eds.), MOLECULAR CLONING: A LABORATORY MANUAL (all from Cold Spring Harbor Laboratory Press); and Hermanson, BIOCONJUGATE TECHNIQUES, 2nd ed. (Academic Press, 2008).

As used herein, "amplifying" generally refers to performing an amplification reaction. As used herein, "amplicon" generally refers to a product of a polynucleotide amplification reaction, which includes a clonal population of polynucleotides, which may be single stranded or double stranded and which may be replicated from one or more starting sequences. In an example, the one or more starting sequences may be one or more copies of the same sequence, or they may be a mixture of different sequences that contain a common region that is amplified such as, for example, a specific exon sequence present in a mixture of DNA fragments extracted from a sample. Amplicons also can be formed by the amplification of a single starting sequence. Amplicons can be produced by a variety of amplification reactions whose products comprise replicates of one or more starting, or target, nucleic acids. Amplification reactions producing amplicons may be "template-driven" in that base pairing of reactants, either nucleotides or oligonucleotides, have complements in a template polynucleotide that are required for the creation of reaction products. Template-driven reactions may be primer extensions with a nucleic acid polymerase or oligonucleotide ligations with a nucleic acid ligase. Such reactions include, for example, polymerase chain reactions (PCRs), linear polymerase reactions, nucleic acid sequence-based amplifications (NASBAs), rolling circle amplifications, for example, or using rolling circle amplification to form a single body that may exclusively occupy a microwell as disclosed in Drmanac et al., U.S. Pat. Appl. Publ. No. 2009/0137404, which is incorporated by reference herein in its entirety. As used herein, "solid phase amplicon" generally refers to a solid phase support, such as a particle or bead, to which is attached a clonal population of nucleic acid sequences, which may have been produced by a emulsion PCR, for example.

As used herein, "analyte" generally refers to a molecule or biological sample that can directly affect an electronic sensor in a region (such as a defined space or reaction confinement region or microwell, for example) or that can indirectly affect such an electronic sensor by a by-product from a reaction involving such molecule or biological cell located in such region. In an embodiment, an analyte may be a sample or template nucleic acid, which may be subjected to a sequencing reaction, which may, in turn, generate a reaction by-product, such as one or more hydrogen ions, that can affect an electronic sensor. The term "analyte" may also encompass multiple copies of analytes, such as proteins, peptides, nucleic acids, for example, attached to solid supports, such as beads or particles. In an embodiment, an analyte may be a nucleic acid amplicon or a solid phase amplicon. A sample nucleic acid template may be associated with a surface via covalent bonding or a specific binding or coupling reaction, and may be derived from, for example, a shot-gun fragmented DNA amplicon library (which are examples of library fragments further discussed herein), or a sample emulsion PCR process creating clonally-amplified sample nucleic acid templates on particles such as Ion-Sphere™ particles. An analyte may include particles having attached thereto clonal populations of DNA fragments, e.g., genomic DNA fragments, cDNA fragments, for example.

As used herein, "primer" generally refers to an oligonucleotide, either natural or synthetic, that is capable, upon forming a duplex with a polynucleotide template, of acting as a point of initiation of nucleic acid synthesis and being extended from, for example, its 3' end along the template so that an extended duplex may be formed. Extension of a primer may be carried out with a nucleic acid polymerase, such as a DNA or RNA polymerase. The sequence of nucleotides added in the extension process may be determined by the sequence of the template polynucleotide. Primers may have a length in the range of from 14 to 40 nucleotides, or in the range of from 18 to 36 nucleotides, for example, or from N to M nucleotides where N is an integer larger than 18 and M is an integer larger than N and smaller than 36. Various embodiments may implement other suitable lengths for primers. Primers may be employed in a variety of amplification reactions, including linear amplification reactions using a single primer, or polymerase chain reactions, employing two or more primers, for example. Guidance for selecting the lengths and sequences of primers may be found in Dieffenbach and Dveksler (eds.), PCR PRIMER: A LABORATORY MANUAL, 2nd ed. (Cold Spring Harbor Laboratory Press, New York, 2003).

As used herein, "polynucleotide" or "oligonucleotide" generally refers to a linear polymer of nucleotide monomers and can be DNA or RNA. Monomers making up polynucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, for example. Such monomers and their internucleosidic linkages may be naturally occurring or may be analogs thereof (e.g., naturally occurring or non-naturally occurring analogs). Non-limiting examples non-naturally occurring analogs include phosphorothioate internucleosidic linkages, bases containing linking groups permitting the attachment of labels, such as fluorophores, or haptens. In an embodiment, oligonucleotide may refer to (relatively) smaller polynucleotides, for example, having 5-40 monomeric units. Polynucleotides may, in some instances, include the natural deoxyribonucleosides (e.g., deoxyadenosine, deoxycytidine, deoxyguanosine, and deoxythymidine for DNA or their ribose counterparts for RNA) linked by phosphodiester linkages. However, they may also include non-natural nucleotide analogs (e.g., including modified bases, sugars, or internucleosidic linkages). In an embodiment, a polynucleotide may be represented by a sequence of letters (upper or lower case), such as "ATGCCTG," and it will be understood that the nucleotides are in 5'→3' order from left to right and that "A" denotes deoxyadenosine, "C" denotes deoxycytidine, "G" denotes deoxyguanosine, and "T" denotes deoxythymidine, and that "I" denotes deoxyinosine, and "U" denotes deoxyuridine, unless otherwise indicated or implied from context. Whenever the use of an oligonucleotide or polynucleotide is associated with enzymatic processing, such as extension by a polymerase or ligation by a ligase, the oligonucleotides or polynucleotides in those instances may not contain certain analogs of internucleosidic linkages, sugar moieties, or bases at any or some positions. Unless otherwise noted the terminology and atom numbering conventions will follow those disclosed in Strachan and Read, HUMAN MOLECULAR GENETICS, 2nd ed. (Wiley-Liss, New York, 1999). Polynucleotides may range in size from a few monomeric units (e.g., 5-40), to several thousand monomeric units, for example.

As used herein, "defined space" (or "reaction space," which may be used interchangeably with "defined space") generally refers to any space or region (which may be in one, two, or three dimensions) in which at least some of a molecule, fluid, and/or solid can be confined, retained and/or localized. In various embodiments, the space may be a predetermined area (which may be a flat area) or volume, and may be defined, for example, by a depression or a micro-machined well in or associated with a microwell plate, microtiter plate, microplate, or a chip. The area or volume may also be determined based on an amount of fluid or solid, for example, deposited on an area or in a volume otherwise defining a space. For example, isolated hydrophobic areas on a generally hydrophobic surface may provide defined spaces. In an embodiment, a defined space may be a reaction chamber, such as a well or a microwell, which may be in a chip. In an embodiment, a defined space may be a substantially flat area on a substrate without wells, for example. A defined space may contain or be exposed to enzymes and reagents used in nucleotide incorporation.

As used herein, "reaction confinement region" or "reaction chamber" generally refers to any region in which a reaction may be confined and includes, for example, a "reaction chamber," a "well," and a "microwell" (each of which may be used interchangeably). A reaction confinement region may include a region in which a physical or chemical attribute of a solid substrate can permit the localization of a reaction of interest. In some embodiments, a reaction confinement region may include a discrete region of a surface of a substrate that can specifically bind an analyte of interest (such as a discrete region with oligonucleotides or antibodies covalently linked to such surface), for example. Reaction confinement regions may be hollow or have well-defined shapes and volumes, which may be manufactured into a substrate. In some embodiments, these latter types of reaction confinement regions may be referred to herein as microwells or reaction chambers, may be fabricated using any suitable microfabrication techniques, and may have volume, shape, aspect ratio (e.g., base width-to-well depth ratio), and other dimensional characteristics that may be selected depending on particular applications, including the nature of reactions taking place as well as the reagents, by-products, and labeling techniques (if any) that are employed. Reaction confinement regions may also be substantially flat areas on a planar surface of a substrate without wells, for example. In various embodiments, microwells may be fabricated using any suitable fabrication technique known in the art. Exemplary configurations (e.g., spacing, shape, and volume) of microwells or reaction chambers are disclosed in Rothberg et al., U.S. Pat. Publ. Nos. 2009/0127589 and 2009/0026082; Rothberg et al., U.K. Pat. Appl. Publ. No. GB 2461127; and Kim et al., U.S. Pat. No. 7,785,862, which are all incorporated by reference in their entirety.

Defined spaces or reaction confinement regions may be arranged as an array, such as, for example, a substantially planar one-dimensional or two-dimensional arrangement of elements such as sensors or wells. The number of columns (or rows) of a two-dimensional array may be the same or may differ. In some embodiments, the array comprises at least 100,000 chambers. Reaction chambers may have a horizontal (lateral or radial) width and a vertical depth that has an aspect ratio of about 1:1 or less, for example. In some embodiments, the pitch between the reaction chambers is no more than about 10 microns and each reaction chamber is no greater than 10 $\mu m^3$ (i.e., 1 pL) in volume, or no greater than 0.34 pL in volume, or no greater than 0.096 pL or, in some instances, 0.012 pL in volume. A reaction chamber may be $2^2$, $3^2$, $4^2$, $5^2$, $6^2$, $7^2$, $8^2$, $9^2$, or $10^2$ square microns in cross-sectional area at the top, for example. In some embodiments, the array may have at least $10^2$, $10^3$, $10^4$, $10^5$, $10^6$, $10^7$, $10^8$, $10^9$, or more reaction chambers, for example. The reaction chambers may be coupled to chemFETs.

Defined spaces or reaction confinement regions, whether arranged as an array or in some other configuration, may be in electrical communication with at least one sensor to allow detection or measurement of one or more detectable or measurable parameter or characteristics. The sensors may convert changes in the presence, concentration, and/or amounts of reaction by-products (or changes in ionic character of reactants) into an output signal, which may be registered electronically, for example, as a change in a voltage level or a current level which, in turn, may be processed to extract information about a chemical reaction or desired association event, for example, a nucleotide incorporation event. The sensors may include at least one chemically sensitive field effect transistor ("chemFET") that can be configured to generate at least one output signal related to a property of a chemical reaction or target analyte of interest in proximity thereof. Such properties can include a concentration (or a change in concentration) of a reactant, product or by-product, or a value of a physical property (or a change in such value), such as an ion concentration. An initial measurement or interrogation of a pH for a defined space or reaction confinement region, for example, may be represented as an electrical signal or a voltage, which may be digitalized (e.g., converted to a digital representation of the electrical signal or the voltage). In various embodiments, these measurements and representations may be considered raw data or a raw signal.

As used herein, "nucleic acid template" (or "sequencing template," which may be used interchangeably with "nucleic acid template") generally refers to a nucleic acid sequence that is a target of one or more nucleic acid sequencing reactions. A sequence for a nucleic acid template may comprise a naturally-occurring or synthetic nucleic acid sequence. A sequence for a nucleic acid template may also include a known or unknown nucleic acid sequence from a sample of interest. In various embodiments, a nucleic acid template may be attached to a solid support such as, e.g., a bead, microparticle, flow cell, or any other surface, support, or object.

As used herein, "fragment library" generally refers to a collection of nucleic acid fragments in which one or more fragments are used as a sequencing template. A fragment library may be generated in numerous ways (e.g., by cutting, shearing, restricting, or otherwise subdividing a larger nucleic acid into smaller fragments). Fragment libraries may be generated or obtained from naturally occurring nucleic acids, such as, for example, from bacteria, cancer cells, normal cells, solid tissue, and the like. Libraries comprising synthetic nucleic acid sequences may also be generated to create a synthetic fragment library.

As used herein, a "molecular sample discriminating code" (or "molecular barcode," which may be used interchangeably with "molecular sample discriminating code") generally refers to an identifiable or resolvable molecular marker, which may be uniquely resolved and may be attached to a sample nucleic acid, biomolecule, or polymer, for example. Such a molecular sample discriminating code may be used for tracking, sorting, separating, and/or identifying sample nucleic acids, biomolecules, or polymers, and may be designed to have properties useful for manipulating nucleic acids, biomolecules, polymers, or other molecules. Molecular sample discriminating codes may comprise the same kind or type of material or subunits comprising the nucleic acid, biomolecule, or polymer they are intended to identify, or they may comprise one or more different material(s) or subunit(s). A molecular sample discriminating code may comprise a short nucleic acid comprising a known, predetermined, or designed sequence. A molecular sample discriminating code may be a nucleic acid sample discriminating code (or nucleic acid barcode), which may be an identifiable or resolvable nucleotide sequence (e.g., an oligonucleotide or polynucleotide sequence). Some example molecular sample discriminating codes may include one or more restriction endonuclease recognition sequences or cleavage sites, overhang ends, adaptor sequences, primer sequences, and the like (including combinations of features or properties). A molecular sample discriminating code may be a biopolymer sample discriminating code, which may include one or more antibody recognition sites, restriction sites, intra- or inert-molecule binding sites, and the like (including combinations of features or properties). A plurality of different molecular sample discriminating codes may be used to identify or characterize samples belonging to a common group, and may be attached to, coupled with, or otherwise associated with libraries (e.g., fragment libraries) of nucleic acids, biomolecules, polymers, or other molecules, for example. In various embodiments, a molecular sample discriminating code or molecular barcode may be represented by a sample discriminating code or sequence or barcode, which may comprise a set of symbols, components, or characters used to represent or define a molecular sample discriminating code or barcode. For example, a sample discriminating code or barcode may comprise a sequence of letters defining a known or predetermined sequence of nucleic acid bases or other biomolecule or polymer constituents. Other embodiments may implement any other suitable symbols and/or alphanumeric characters other than letters. Sample discriminating codes or barcodes may be used in a variety of sets, subsets, and groupings, for example as part of a sequencing run or in order to accomplish multiplexing. Sample discriminating codes or barcodes may be read, or otherwise recognized, identified, or interpreted as a function of a sequence or other arrangement or relationship of subunits that together form a motif. In some embodiments, the sample discriminating codes may comprise a series of signals output by a sequencing instrument when sequencing the barcode according to a predetermined flow order (e.g., a flowspace over a barcode), as further detailed herein. In some embodiments, sample discriminating codes or barcodes may also contain one or more additional functional elements including key sequences for quality control and sample detection, primer sites, adaptors for ligation, linkers for attaching to substrates, inserts, and any other suitable elements.

FIG. 1 is a block diagram illustrating components of an exemplary system for nucleic acid sequencing that may be implemented with various embodiments. The components include a flow cell comprising a sensor array 100, a reference electrode 108, a plurality of reagents 114, a valve block 116, a wash solution 110, a valve 112, a fluidics controller 118, fluid lines 120/122/126, passages 104/109/111, a waste container 106, an array controller 124, and a user interface 128. The flow cell and sensor array 100 includes an inlet 102, an outlet 103, a reaction chamber array 107 positioned in a flow chamber 105 that defines a flow path of reagents over the reaction chamber array 107. The reference electrode 108 may be of any suitable type or shape, including a concentric cylinder with a fluid passage or a wire inserted into a lumen of passage 111. The reagents 114 may be driven through the fluid pathways, valves, and flow cell by pumps, gas pressure, or other suitable methods, and may be discarded into the waste container 106 after exiting the flow cell and sensor array 100.

In some embodiments, reagents 114 may, for example, contain dNTPs to be flowed through passages 130 and through the valve block 116, which may control the flow of the reagents 114 to flow chamber 105 via passage 109. The reservoir 110 may contain a wash solution used to wash away dNTPs, for example, that may have previously been flowed. The reaction chamber array 107 may include an array of defined spaces or reaction confinement regions, such as wells or microwells, for example, that is operationally associated with a sensor array so that, for example, each reaction chamber is associated with a sensor suitable for detecting an analyte or reaction property of interest that results from a reaction taking place in the reaction chamber. The reaction chamber 107 may be integrated with the sensor array as a single device or chip. The flow cell may have a variety of designs for controlling the path and flow rate of reagents over the reaction chamber array 107, and may be a microfluidics device. The array controller 124 may provide bias voltages and timing and control signals to the sensor, and collect and/or process output signals. The user interface 128 may display information from the flow cell and sensor array 100 as well as instrument settings and controls, and allow a user to enter or set instrument settings and controls.

In some embodiments, the system may be configured to let a single fluid or reagent contact the reference electrode 108 throughout a multi-step reaction. The valve 112 may be shut to prevent wash solution 110 from flowing into passage 109 as the reagents are flowing. Although the flow of wash solution may be stopped, there may still be uninterrupted fluid and electrical communication between the reference electrode 108, passage 109, and the sensor array 107. The distance between the reference electrode 108 and the junction between passages 109 and 111 may be selected so that little or no amount of the reagents flowing in passage 109 and possibly diffusing into passage 111 reach the reference electrode 108. In an embodiment, the wash solution 110 may be selected as being in continuous contact with the reference electrode 108. In an example, such a configuration may be useful for multi-step reactions using frequent wash steps. In various embodiments, the fluidics controller 118 may be programmed to control driving forces for flowing reagents 114 and the operation of valve 112 and valve block 116 with any suitable instrument control software, such as LabView (National Instruments, Austin, Tex.), to deliver reagents to the flow cell and sensor array 100 according to a predetermined reagent flow ordering. The reagents may be delivered for predetermined durations, at predetermined flow rates, and may measure physical and/or chemical parameters providing information about the status of one or more reactions taking place in defined spaces or reaction confinement regions, such as, for example, wells or microwells.

Figure 2A:
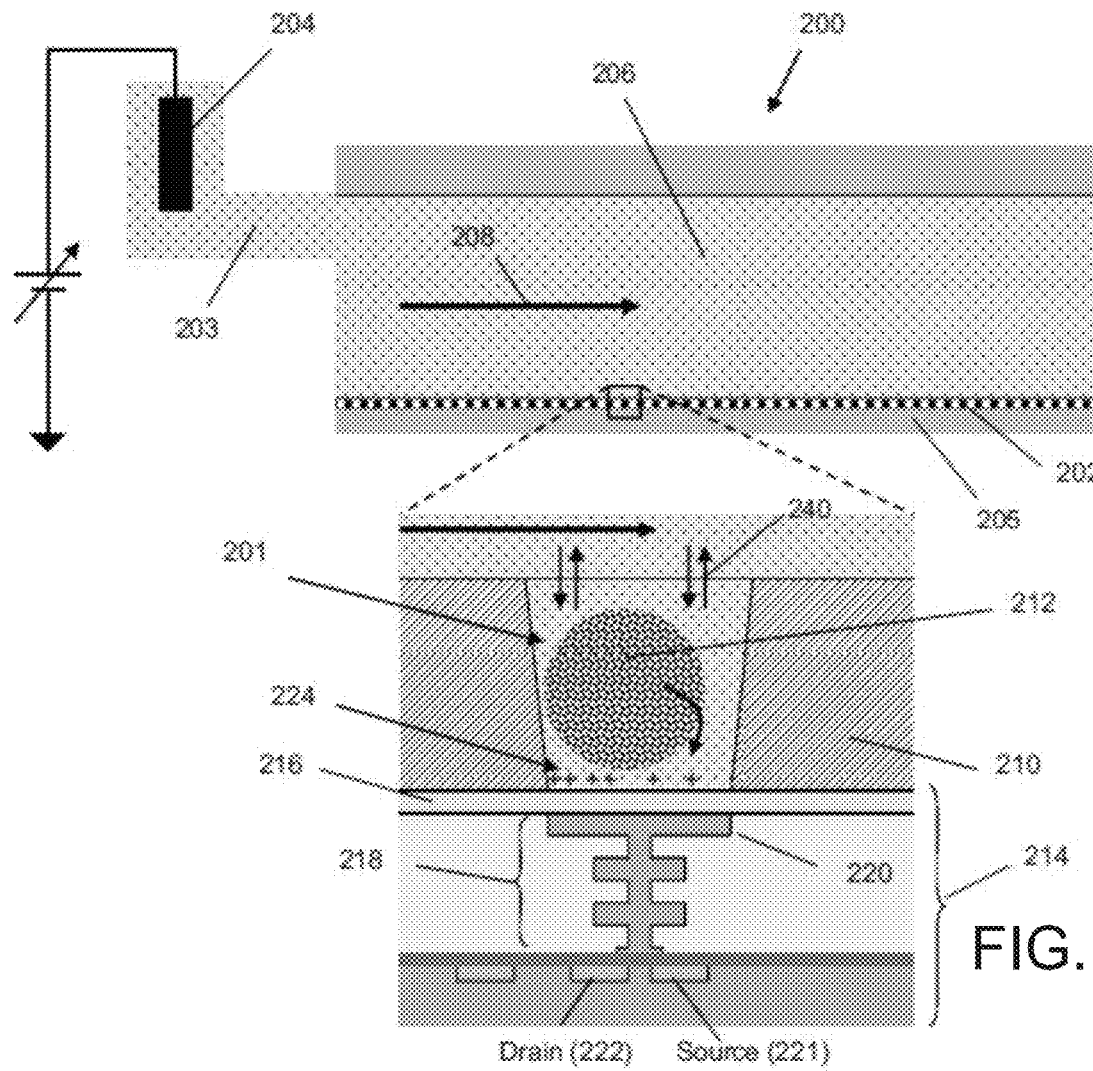
FIG. 2A illustrates cross-sectional and detailed views of an exemplary flow cell for nucleic acid sequencing.

FIG. 2A illustrates cross-sectional and detailed views of an exemplary flow cell 200, such as may be used in the system of FIG. 1, for nucleic acid sequencing in accordance with various embodiments. The flow cell 200 may include a reaction chamber array 202, a sensor array 205, and a flow chamber 206 in which a reagent flow 208 can move across a surface of the reaction chamber array 202, over open ends of the reaction chambers in the reaction chamber array 202. The flow of reagents (e.g., dNTPs) can be provided in any suitable manner, including delivery by pipettes, or through tubes or passages connected to a flow chamber. The duration, concentration, and/or other flow parameters may be the same or different for each reagent flow. Likewise, the duration, composition, and/or concentration for each wash flow may be the same or different.

Reaction chambers in the reaction chamber array 202 may have any suitable volume, shape, and aspect ratio, which may be selected depending on one or more of any reagents, by-products, and labeling techniques used, and the reaction chambers may be formed in a layer 210, for example, using any suitable fabrication or microfabrication technique. With reference to the detailed view of FIG. 2A, a reaction chamber 201 may be in the form of a well, a microwell, a throughhole, surface portion having relative liquid affinity to act as a confinement region, or any other suitable containment structure. A sensor 214 in the sensor array 205 may be an ion sensitive (ISFET) or a chemical sensitive (chemFET) sensor with a floating gate 218 having a sensor plate 220 separated from the reaction chamber interior by a passivation layer 216. The sensor 214 responsive to (and can generate an output signal related to) an amount of charge 224 present on the passivation layer 216 opposite of the sensor plate 220. Changes in the amount of charge 224 cause changes in the current between a source 221 and a drain 222 of the sensor 214, which may be used directly to provide a current-based output signal or indirectly with additional circuitry to provide a voltage-based output signal. Reactants, wash solutions, and other reagents may move into reaction chamber, for instance by diffusion 240, as those substances are flowed through reaction chamber 206. One or more analytical reactions to identify or determine characteristics or properties of an analyte of interest may be carried out in one or more reaction chambers 201 of the reaction chamber array 202.

In some embodiments, such reactions generate, directly or indirectly, by-products that affect the amount of charge 224 in sensing proximity of (e.g., adjacent to) the sensor plate 220. In an embodiment, a reference electrode 204 may be fluidically connected to the flow chamber 206 via a flow passage 203. In an embodiment, the reaction chamber array 202 and the sensor array 205 together form an integrated unit forming a bottom wall or floor of the flow cell 200. In an embodiment, one or more copies of an analyte is attached to a solid phase support 212, which can include microparticles, nanoparticles, beads, gels, and be solid and porous, for example. The analyte may include a nucleic acid analyte, including a single copy and multiple copies, and may be made, for example, by rolling circle amplification (RCA), exponential RCA, or other suitable techniques to produce an amplicon without the need of a solid support.

Figure 2B:
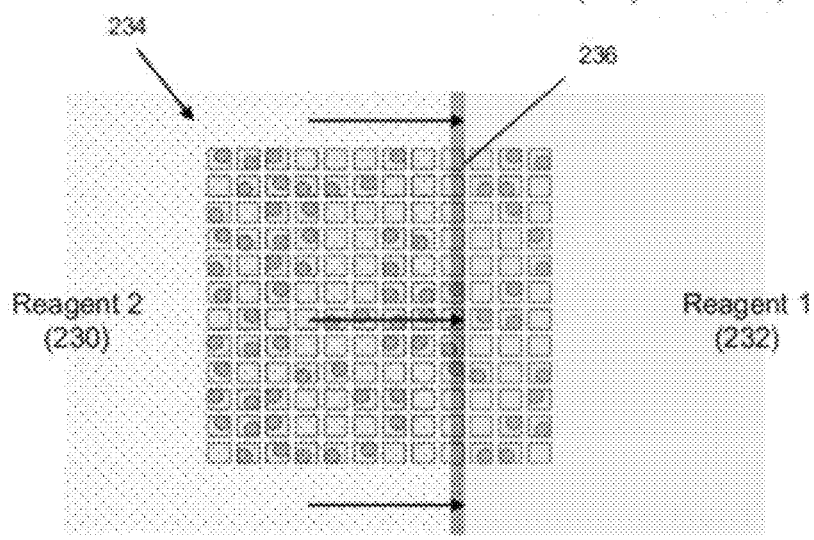
FIG. 2B illustrates an exemplary uniform flow front between successive reagents moving across a section of an exemplary reaction chamber array.

FIG. 2B schematically illustrates an exemplary uniform flow front between successive reagents moving across a section 234 of an exemplary reaction chamber array in accordance with various embodiments. A "uniform flow front" between first reagent 232 and second reagent 230 refers to the reagents undergoing little or no mixing as they move, thereby establishing a narrow, discernable boundary 236 between them. The boundary may be generally linear for flow cells having inlets and outlets at opposite ends of their flow chambers, or it may be curvilinear for flow cells having central inlets (or outlets) and peripheral outlets (or inlets). In an embodiment, the flow cell design and reagent flow rate may be selected so that each newly introduced reagent flows with a uniform flow front as it transits the flow chamber during a switch from one reagent to another.

Figure 3:
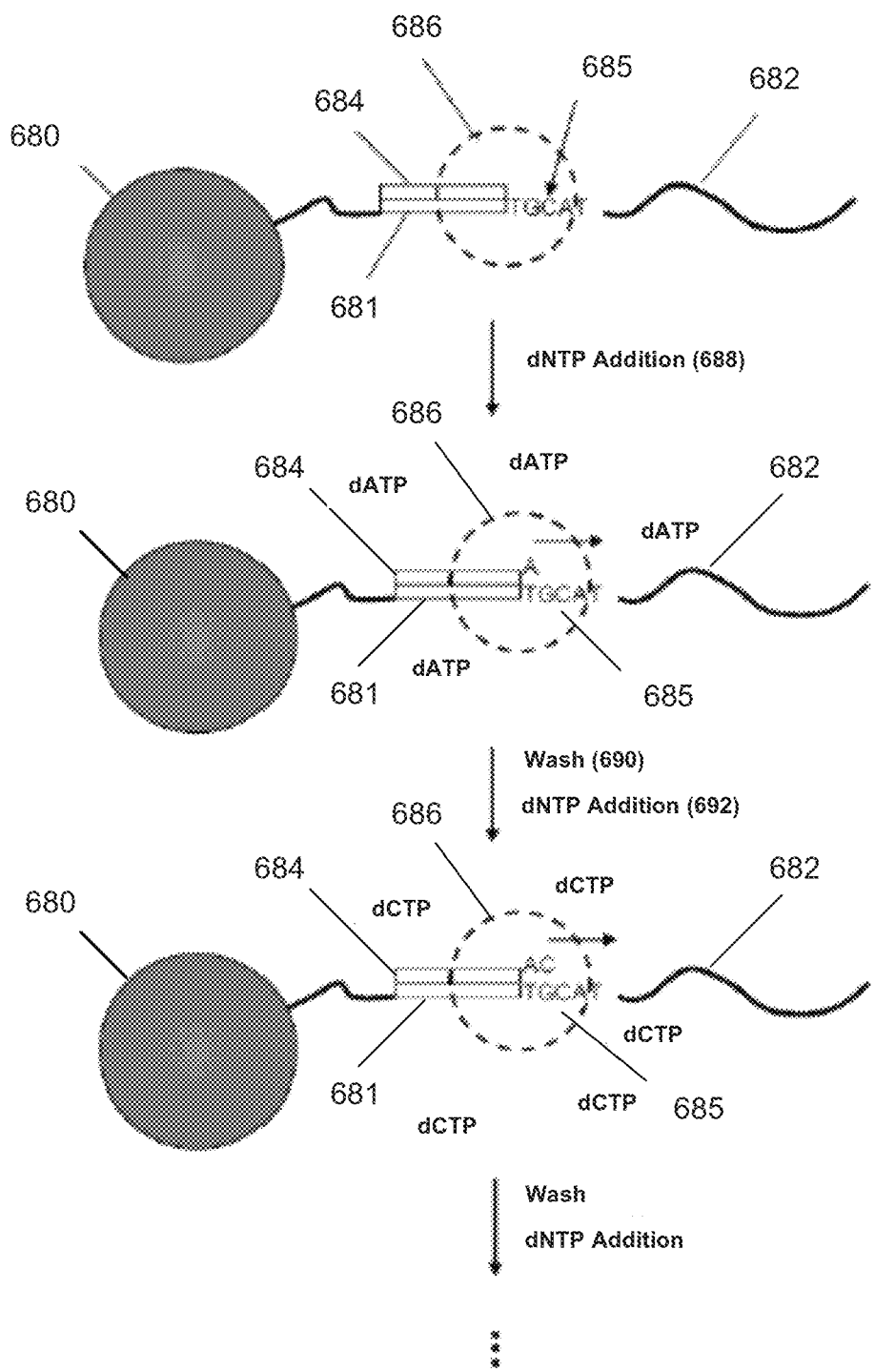
FIG. 3 illustrates an exemplary process for label-free, pH-based sequencing.

FIG. 3 illustrates an exemplary process for label-free, pH-based sequencing in accordance with various embodiments. A template 682 with sequence 685 and a primer binding site 681 are attached to a solid phase support 680. The template 682 may be attached as a clonal population to a solid support, such as a microparticle or bead, for example, and may be prepared as disclosed in Leamon et al., U.S. Pat. No. 7,323,305, which is incorporated by reference herein in its entirety. In an embodiment, the template may be associated with a substrate surface or present in a liquid phase with or without being coupled to a support. A primer 684 and DNA polymerase 686 are operably bound to the template 682. As used herein, "operably bound" generally refers to a primer being annealed to a template so that the primer's 3' end can be extended by a polymerase and that a polymerase is bound to such primer-template duplex (or in close proximity thereof) so that binding and/or extension can take place when dNTPs are added.

In step 688, dNTP (shown as dATP) is added, and the DNA polymerase 686 incorporates a nucleotide "A" because "T" is the next nucleotide in the template 682 and is complementary to the flowed dATP nucleotide. In step 690, a wash is performed in accordance with descriptions presented herein, and is followed by step 692, in which the next dNTP (shown as dCTP) is added, and the DNA polymerase 686 incorporates a nucleotide "C" because "G" is the next nucleotide in the template 682. The pH-based nucleic acid sequencing, in which base incorporations are determined by measuring hydrogen ions that are generated as natural by-products of polymerase-catalyzed extension reactions, may be performed using at least in part one or more features of Anderson et al., A SYSTEM FOR MULTIPLEXED DIRECT ELECTRICAL DETECTION OF DNA SYNTHESIS, Sensors and Actuators B: Chem., 129:79-86 (2008); Rothberg et al., U.S. Pat. Appl. Publ. No. 2009/0026082; and Pourmand et al., DIRECT ELECTRICAL DETECTION OF DNA SYNTHESIS, Proc. Natl. Acad. Sci., 103:6466-6470 (2006), which are all incorporated by reference herein in their entirety. In an embodiment, after each addition of a dNTP, an additional step may be performed in which the reaction chambers are treated with a dNTP-destroying agent, such as apyrase, to eliminate any residual dNTPs remaining in the chamber that might result in spurious extensions in subsequent cycles.

In an embodiment, the primer-template-polymerase complex may be subjected to a series of exposures of different nucleotides in a predetermined or known sequence or ordering. When one or more nucleotides are incorporated, then the signal resulting from the incorporation reaction may be detected, and after repeated cycles of nucleotide addition, primer extension, and signal acquisition, the nucleotide sequence of the template strand can be determined. In an example, the output signals measured throughout this process depend on the number of nucleotide incorporations. In particular, in each additional sequencing step, the polymerase extends the primer by incorporating added dNTP when the next base in the template is complementary to the added dNTP. If there is one complementary base, there is one incorporation; if two, there are two incorporations; if three, there are three incorporations, and so on. With each incorporation, a hydrogen ion is released, and collectively a population of released hydrogen ions changes the local pH of the contents contained in the reaction chamber.

In an embodiment, the production of hydrogen ions is monotonically related to the number of contiguous complementary bases in the template (as well as to the total number of template molecules with primer and polymerase that participate in an extension reaction). Thus, when there is a number of contiguous identical complementary bases in the template (which may represent a homopolymer region), the number of hydrogen ions generated and thus the magnitude of the local pH change is proportional to the number of contiguous identical complementary bases (and the corresponding output signals are then sometimes referred to as "1-mer," "2-mer," "3-mer" output signals, etc.). If the next base in the template is not complementary to the added dNTP, then no incorporation occurs and no hydrogen ion is released (and the output signal is then sometimes referred to as a "0-mer" output signal). In some examples, in each wash step of the cycle, an unbuffered wash solution at a predetermined pH may be used to remove the dNTP of the previous step in order to prevent misincorporations in later cycles. Deliveries of nucleotides to a reaction vessel or chamber may be referred to as "flows" of nucleotide triphosphates (or dNTPs). For convenience, a flow of dATP will sometimes be referred to as "a flow of A" or "an A flow." Also, a sequence of flows may be represented as a sequence of letters, such as "ATGT" indicating a flow of dATP, followed by a flow of dTTP, followed by a flow of dGTP, followed by a flow of dTTP.

In an embodiment, the four different kinds of dNTP are added sequentially to the reaction chambers, so that each reaction is exposed to the four different dNTPs, one at a time. In an embodiment, the four different kinds of dNTP are added in the following sequence: dATP, dCTP, dGTP, dTTP, dATP, dCTP, dGTP, dTTP, etc., with the exposure, incorporation, and detection steps followed by a wash step. The exposure to a nucleotide followed by a washing step can be considered a "nucleotide flow." In some examples, four consecutive nucleotide flows can be considered a "cycle." For example, a two cycle nucleotide flow order can be represented by: dATP, dCTP, dGTP, dTTP, dATP, dCTP, dGTP, dTTP, with each exposure being followed by a wash step. Different flow orders may be implemented, as further detailed herein. In various embodiments, the predetermined sequence or ordering may be based on a cyclical, repeating pattern of consecutive repeats of a predetermined reagent flow ordering (e.g., consecutive repeats of predetermined sequence of four nucleotide reagents such as "TACG TACG . . . "), or may be based on a random reagent flow ordering, or may be based on an ordering comprising in whole or in part a phase-protecting reagent flow ordering as described in Hubbell et al., U.S. patent application Ser. No. 13/440,849, published Oct. 28, 2012 as U.S. Patent Pub. No. 2012/0264621, entitled PHASE-PROTECTING REAGENT FLOW ORDERINGS FOR USE IN SEQUENCING-BY-SYNTHESIS, which is incorporated by reference herein in its entirety, or some combination thereof. In other embodiments, labeled pH-based sequencing may be implemented in a similar manner.

Figure 4:
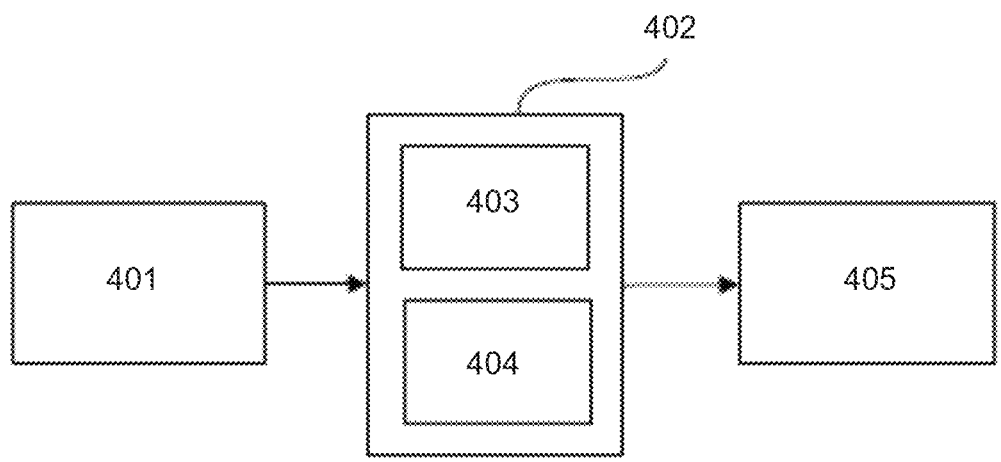
FIG. 4 is a block diagram illustrating an exemplary system for obtaining, processing, and/or analyzing multiplex nucleic acid sequencing data.

FIG. 4 is a block diagram illustrating an exemplary system for obtaining, processing, and/or analyzing multiplex nucleic acid sequencing data in accordance with various exemplary embodiments. The system includes a sequencing instrument 401, a server 402, and one or more end user computers 405. The sequencing instrument 401 may be configured to process samples comprising barcodes and to deliver reagents according to a predetermined ordering as detailed herein. The predetermined ordering may be based on a cyclical, repeating pattern of consecutive repeats of a predetermined reagent flow ordering (e.g., consecutive repeats of predetermined sequence of four nucleotide reagents such as "TACG TACG . . . "), or may be based on a random reagent flow ordering, or may be based on an ordering comprising in whole or in part a phase-protecting reagent flow ordering, or some combination thereof. In an embodiment, the barcodes may be determined at least in part as a function of the ordering. For example, the barcodes may comprise sequence motif designed barcodes that are designed in accordance with a predetermined flow ordering, as further described herein. Exemplary sequencing instruments that can be used in conjunction with the barcodes of the present disclosure include, but are not limited to, for example, Ion PGM™, Ion Proton™, Ion S5™ and Ion S5 XL Next Generation™ Sequencing System. Persons having ordinary skill in the art would appreciate that other sequencing instruments and platforms, such as, for example, various fluorophore-labeled nucleotide sequencing platforms, also may be used in conjunction with the barcodes of the present disclosure.

The server 402 may include a processor 403 and a memory and/or database 404. The sequencing instrument 401 and the server 402 may include one or more computer readable media for obtaining, processing, and/or analyzing multiplex nucleic acid sequencing data. In an embodiment, the instrument and the server or other computing means or resource may be configured as a single component. One or more of these components may be used to perform all or parts the embodiments described herein.

In various exemplary embodiments, a sequence may be determined and/or one or more nucleic acid samples may be identified using sequencing-by-synthesis. In sequencing-by-synthesis, the sequence of a target nucleic acid is determined by the stepwise synthesis of complementary nucleic acid strands on a target nucleic acid (whose sequence and/or identity is to be determined) serving as a template for the synthesis reactions (e.g., by a polymerase extension reaction that typically includes the formation of a complex comprising a template or target polynucleotide), a primer annealed thereto, and a polymerase operably coupled or associated with the primer-template hybrid so as to be capable of incorporating a nucleotide species (e.g., a nucleoside triphosphate, a nucleotide triphosphate, a precursor nucleoside or nucleotide) to the primer). During sequencing-by-synthesis, nucleotides can be sequentially added to growing polynucleotide molecules or strands at positions complementary to template polynucleotide molecules or strands. The addition of the nucleotides to the growing complementary strandscan be detected using a variety of methods (e.g., pyrosequencing, fluorescence detection, and label-free electronic detection, and the like), and the identity of the sequence composition of the template nucleic acid determined from the detection. This process may be iterated until a complete or selected sequence length complementary to the template has been synthesized.

As noted above, in various embodiments, data and signals that are generated, processed, and/or analyzed can be obtained using electronic or charged-based nucleic acid sequencing. In electronic or charged-based sequencing (e.g., pH-based sequencing), a nucleotide incorporation event is determined by detecting ions (e.g., hydrogen ions) generated as natural by-products of polymerase-catalyzed nucleotide extension reactions. This may be used to sequence a sample or template nucleic acid, which may be a fragment of a nucleic acid sequence of interest, for example, and which may be directly or indirectly attached as a clonal population to a solid support, such as a particle, microparticle, bead, or the like. The sample or template nucleic acid can be operably associated to a primer and polymerase and subjected to repeated cycles or "flows" of deoxynucleoside triphosphate ("dNTP") addition and washing. The primer may be annealed to the sample or template so that the primer's 3' end can be extended by a polymerase whenever dNTPs complementary to the next base in the template are added. Based on the known sequence of flows and on measured signals indicative of ion concentration during each nucleotide flow, the identity of the type, sequence and number of nucleotide(s) associated with a sample nucleic acid present in a reaction chamber is determined.

Figure 5:
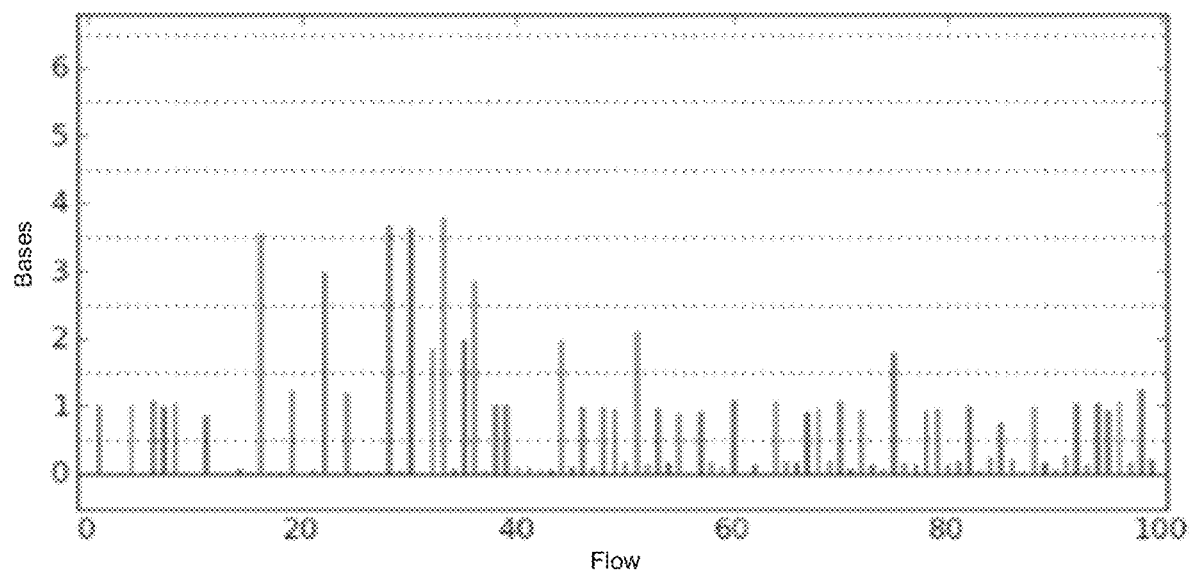
FIG. 5 shows an exemplary ionogram representation of signals from which base calls may be made.

FIG. 5 shows an exemplary ionogram representation of signals from which base calls can be made. In this example, the x-axis shows the nucleotide that is flowed and the corresponding number of nucleotide incorporations may be estimated by rounding to the nearest integer shown in the y-axis, for example. Signals used to make base calls and determine sequencing data (e.g., a flowspace vector) may be from any suitable point in the acquisition or processing of the data signals received from sequencing operations. For example, the signals may be raw acquisition data or data having been processed (e.g., by background filtering, normalization, correction for signal decay, and/or correction for phase errors or effects, and the like). The base calls may be made by analyzing any suitable signal characteristics (e.g., signal amplitude, intensity, and the like).

In various embodiments, output signals due to nucleotide incorporation may be further processed, given knowledge of the predetermined nucleotide species that were flowed and in what order to obtain such signals, to make base calls for the flows and compile consecutive base calls associated with a sample nucleic acid template into a read. A base call refers to a particular nucleotide identification (e.g., dATP ("A"), dCTP ("C"), dGTP ("G"), or dTTP ("T")). Base calling may include performing one or more signal normalizations, signal phase and signal droop (e.g, enzyme efficiency loss) estimations, and signal corrections, and may identify or estimate base calls for each flow for each defined space. Base calling may include performing or implementing one or more of the teachings disclosed in Davey et al., U.S. patent application Ser. No. 13/283,320, published May 3, 2012 as U.S. Patent Pub. No. 2012/0109598, entitled PREDICTIVE MODEL FOR USE IN SEQUENCING-BY-SYNTHESIS, which is incorporated by reference herein in its entirety. Other aspects of signal processing and base calling may include performing or implementing one or more of the teachings disclosed in Davey et al., U.S. patent application Ser. No. 13/340,490, published Jul. 5, 2012 as U.S. Patent Pub. No. 2012/0173159, entitled METHOD, SYSTEM, AND COMPUTER READABLE MEDIA FOR NUCLEIC ACID SEQUENCING, and Sikora et al., U.S. patent application Ser. No. 13/588,408, published Mar. 7, 2013 as U.S. Patent Pub. No. 2013/0060482, entitled METHOD, SYSTEM, AND COMPUTER READABLE MEDIA FOR MAKING BASE CALLS IN NUCLEIC ACID SEQUENCING, which are all incorporated by reference herein in their entirety.

Barcodes

In various embodiments, sample discriminating codes or barcodes may comprise or correspond to or with (whether directly or indirectly) sequences of nucleotides, biomolecule components and/or subunits, or polymer components and/or subunits. In an embodiment, a sample discriminating code or barcode may correspond to a sequence of individual nucleotides in a nucleic acid or subunits of a biomolecule or polymer or to sets, groups, or continuous or discontinuous sequences of such nucleotides or subunits. In an embodiment, a sample discriminating code or barcode may also correspond to or with (whether directly or indirectly) transitions between nucleotides, biomolecule subunits, or polymer subunits, or other relationships between subunits forming a sample discriminating code or barcode (e.g., adaptors, key bases, and the like).

In various embodiments, sample discriminating codes or barcodes have properties that permit them to be sequenced, or otherwise recognized, identified, or interpreted with improved accuracy and/or reduced error rates for a given code type, length, or complexity. In an embodiment, a sample discriminating code or barcode is designed as a set (which may include subsets) of individual sample discriminating codes or barcodes. In some embodiments, one or more sample discriminating codes or barcodes in a set (or in a subset from that set) are selected based on one or more criteria to improve accuracy and/or reduce error rates in reading, or otherwise recognizing, identifying, discriminating, or interpreting the codes.

In various embodiments, sample discriminating codes or barcodes are be designed to exhibit high fidelity reads that can be assessed based on empirical sequencing measurements. The level of fidelity may be based on predictions of the read accuracy of a sample discriminating code or barcode having a particular nucleotide sequence. Certain nucleotide sequences known to cause sequencing read ambiguity, errors, or sequencing bias may be avoided. Design may be based on accurately calling the sample discriminating code or barcode (and associated sample or nucleic acid population), even in the presence of one or more errors. In various embodiments, fidelity may be based on the probability of correctly sequencing the sample discriminating code or barcode, which may be at least 82%, or at least 85%, or at least 90%, or at least 95%, or at least 99%, or more.

In various embodiments, sample discriminating codes or barcodes may be designed to exhibit improved read accuracy for sequencing using a sequence-by-synthesis platform (as discussed previously), which may include fluorophore-labeled nucleotide sequencing platforms or non-labeled sequencing platforms, such as, for example, the Ion PGM™ and Ion Proton™ Sequencers, and the Ion S5™ and Ion S5 XL Next Generation™ Sequencing System. Design of the sample discriminating codes or barcodes and specific sequences are not limited to any particular instrument platform or sequencing technology, however. In the case of non-nucleic acid codes, sample discriminating codes or barcodes may be sequences, identified, interpreted or otherwise recognized using methods known in the art, including for example, amino acid sequencing for protein sample discriminating codes.

In some embodiments, sample barcodes comprise combinatorial barcodes that comprise a combination of a sequence motif. For example, a sequence motif may be determined, and a sample barcode can comprise a combination of two or more repeats of the sequence motif. Such a combinatorial sequence for the barcodes can allow a high number of barcodes to be generated (e.g., over one million) and further benefit from design advantages that stem from the sequence motif.

In various embodiments, a sequence motif comprises a design or pattern for a predetermined number of nucleotide bases (e.g., 2, 3, 4, 5, or more). For example, a sequence motif of the length 3 can comprise a first group of nucleotides, a second group of nucleotides, and a third group of nucleotides, the first, second, and third groups being different from one another. In this example, a first nucleotide base for the barcode may be selected from the first group, a second nucleotide base may be selected from the second group, and a third nucleotide base may be selected from the third group. In an instance where the barcode length is 6 nucleotide bases, the sequence motif may be repeated once. For example, the fourth nucleotide base for the barcode may be selected from the first group, the fifth nucleotide base may be selected from the second group, and the sixth nucleotide base may be selected from the third group. Such a barcode would be represented as [first group][second group][third group][first group][second group][third group], where the barcode has a length of 6 nucleotide bases. In other embodiments, the sequence motif may be of a different length and the pattern for the sequence motif may be repeated 2, 3, 4, or more times such that the barcode may comprise any other suitable length.

Figure 6A:
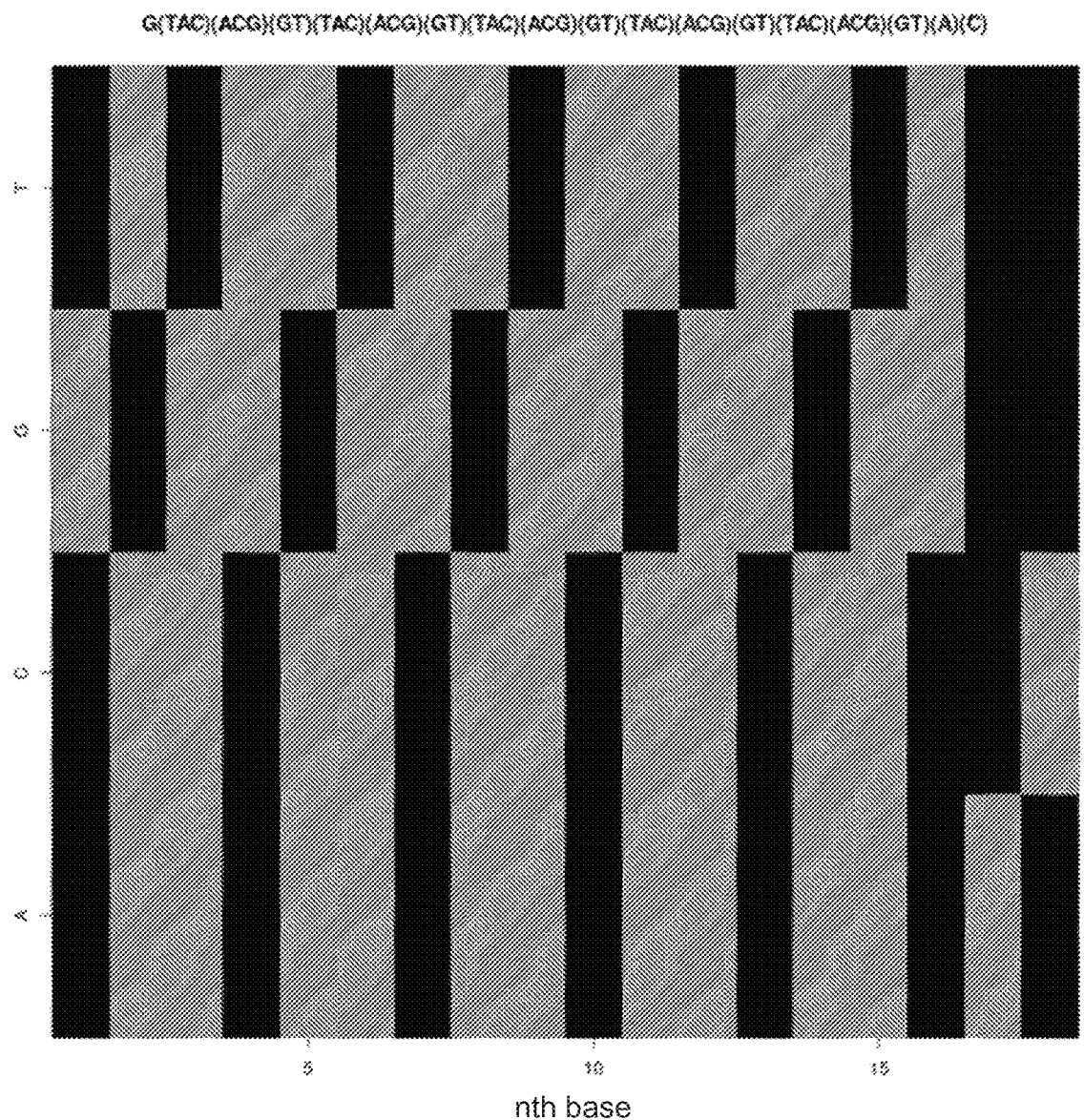
FIGS. 6A and 6B illustrate plots related to combinatorial barcode sequences.

In some embodiments, design criteria is determined for the design of a combinatorial barcode sequence. Example criteria include, but are not limited to: a potential to generate millions of barcodes, flow synchronization over the generated barcodes, and barcodes that do not include long homopolymers (e.g., over a threshold length, such as 3, 4, or more bases). One example of a sequence motif that satisfies such a criteria is the design [HVK](n), where [H], [V], and [K] indicate groups of nucleotides and (n) indicates a number of repetitions for the sequence motif. For example, [H] may be the group of bases [T A C], [V] may be the group of bases [A C G], and [K] may be the group of bases [G T]. Accordingly, another notation for the sequence motif may be [T A C][A C G][G T](n). This exemplary sequence motif is of length 3, and each 3 base iteration includes 18 potential combinations (e.g., 3×3×2). Therefore, the number of potential barcodes generated using the motif is a function of (n), namely 18^n. For instance, where n=5, the number of potential barcodes is about 1.9 million. In addition, the [H][V][K] combinatorial ordering for the designed barcode ensures that no homopolymer of length greater than 2 is generated, regardless of the number of repetitions, at least because the potential combinations of bases, and thus the potential order of bases, is known. FIG. 6A illustrates a plot of possible combinations of nucleotide bases for the sequence motif [H][V][K](n).

The sequence motif's combinatorial ordering also provides the possibility for a synchronized flow order. For instance, given a predetermined flow ordering that is based on the sequence motif and order for the groups of bases of the sequence motif, the barcodes may be expected to complete sequencing within the same flow (or two flows). For example, given the [H][V][K] order for the above sequence motif, or [T A C][A C G][G T] the, barcodes generated from a combination of this motif would be expected to synchronize over the predetermined flow orders [T C A C G](n)[T] or [T A C A G](n)[T]. The order of the nucleotide flows for these two flow orders corresponds to the potential combinations of bases within any barcode sequence generated from combinations of the sequence motif [H][V][K]. As such, given any of the two flow orders and plurality of barcodes generated from the sequence motif [H][V][K](5) (SEQ ID NO: 1), the barcodes would be expected to synchronize (end sequencing) over the pair of flows G T of the flow orders. The predetermined flow order, or flow order motif, may be repeated in accordance with the number of iterations for the sequence motif to sequence the length of the combinatorial barcode sequence.

Figure 6B:
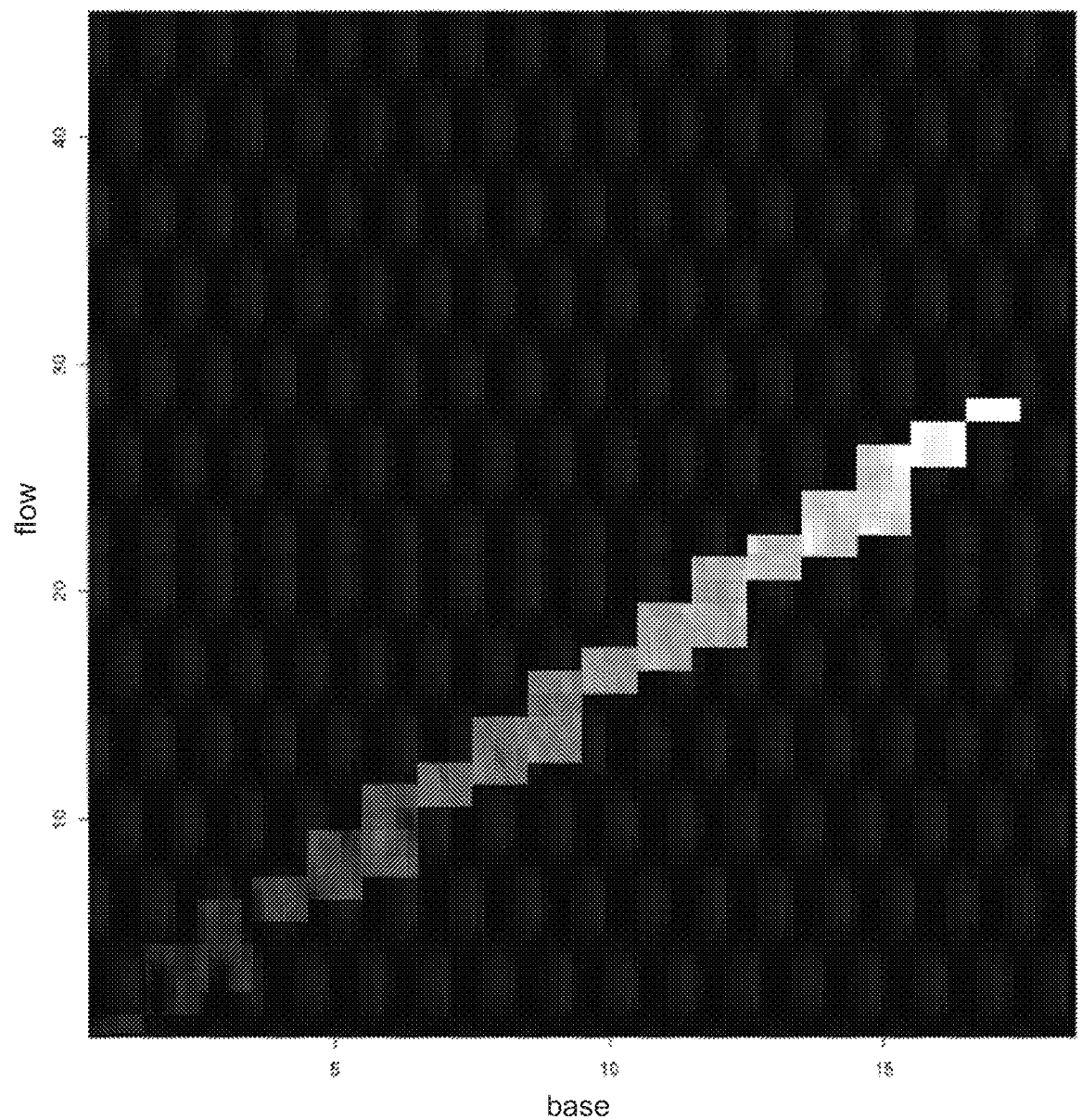

In an embodiment, the sequence motif [H][V][K](5) (SEQ ID NO: 1) coupled with the flow order [T C A C G](n)[T] or [T A C A G](n)[T] would meet the above-indicated design criteria. That is, the sequence motif generates 1.9 million potential barcodes, provides flow synchronization when coupled with the predetermined flow orders, and limits homopolymer length to no longer than 2. FIG. 6B illustrates a plot of the sequence motif [H][V][K](5) (SEQ ID NO: 1) with two stuffer nucleotide bases that displays the flow synchronization of the 1.9 million potential barcodes generated.

In some embodiments, the scale for barcodes generated by a sequence motif is be increased (e.g., doubled) based on the nucleotide base appended to the barcode directly preceding it. For example, the [H][V][K](5) (SEQ ID NO: 1) sequence motif begins with one of three bases, T A or C, but not the base G. Accordingly, adding a combination to the generated combinatorial barcodes that includes a G to start the barcode can double the number. For example, a library identification code may precede the barcode in a read structure, and the library identification code may end in the base G. Because the initial base G does not interfere with the [H] that begins the sequence motif, the barcodes would still be expected to cleanly synchronize when starting the flow order.

In various embodiments, other potential sequence motifs may be implemented to generate combinatorial barcodes that meet various other design criteria. For example, a sequence motif may be defined by the design [T A C][A C G][C G T][G T A](n). Here the sequence motif is of length 4 bases, and there are 84 possible combinations given the order and groupings (3×3×3×3). The number of potential barcodes generated is a function of n, 84^n. A predetermined flow order that corresponds to the sequence motif, based on the potential combination of bases generated by the sequence motif, may be [T C][A G][C T][G A](n)[T]. Using the predetermined flow order, any potential barcode generated from the sequence motif is expected to complete sequencing within the flows, however some generated barcode sequences may complete early (e.g., before the terminating T flow). Given the potential ordering for bases, the sequence motif limits homopolymer length to no more than 3.

In various embodiments, other potential sequence motifs can be implemented to generate combinatorial barcodes that meet various other design criteria. For example, a sequence motif may be defined by the design [T A][A C][C G][G T](n). Here the sequence motif is of length 4 bases, and there are 16 possible combinations given the order and groupings (2×2×2×2). The number of potential barcodes generated is a function of n, 16^n. A predetermined flow order that corresponds to the sequence motif, based on the potential combination of bases generated by the sequence motif, may be [T A C G](n)[T]. Using the predetermined flow order, any potential barcode generated from the sequence motif is expected to be flow synchronized (e.g., not expected to complete early). Given the potential ordering for bases, the sequence motif limits homopolymer length to no more than 2.

Figure 7:
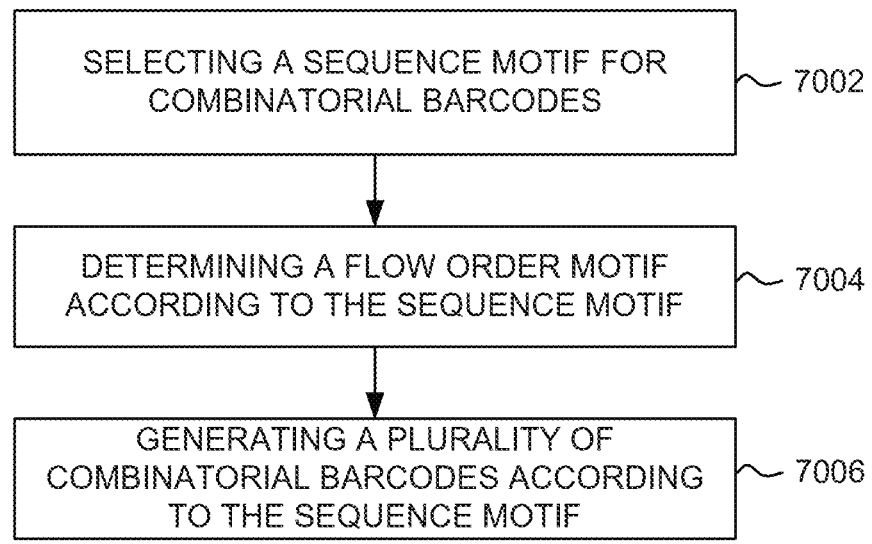
FIG. 7 illustrates an exemplary method for generating combinatorial barcode sequences.

FIG. 7 illustrates a exemplary parts of a workflow for generating a plurality of combinatorial barcodes according to various embodiments. For example, at step 702 a sequence motif is selected for the combinatorial barcodes. The sequence motif may be selected based on one or more design criteria for the barcodes, such as potential number of barcodes generated, desired homopolymer length, flow synchronization attributes, and the like. Any of the described sequence motifs or any other suitable sequence motif can be selected. At step 704, a flow order motif for the sequence motif is determined. For example, based on the sequence motif selected, a flow order to be used to sequence the generated barcode that is a combination of the selected sequence motif is determined. The flow order motif may be selected such that sequencing over any barcode of the selected sequence motif is synchronized. At step 706, the plurality of combinatorial barcodes is generated according to the selected sequence motif. For example, a plurality of barcode sequences that are various combinations of the selected sequence motif can be manufactured. The manufactured barcodes may number in the millions, such as 1.9 million, 3.8 million, or any other suitable number.

In various embodiments, combinatorial barcodes are bound to a target sequence or insert, and in such cases they assist in uniquely identifying or discriminating different target sequences. The target sequence can be any type of sequence from any source of interest, including, but not limited to, amplicons, candidate genes, mutational hot spots, single nucleotide polymorphisms, genomic library fragments, for example. The combinatorial barcode sequence can be operatively coupled to the target sequence at any of various points in the sample preparation process using techniques such as, for example, PCR amplification, DNA ligation, bacterial cloning, and other suitable techniques. The combinatorial barcode sequence may be contained in oligonucleotides and ligated to genomic library fragments using any suitable DNA ligation technique.

Figure 8A:
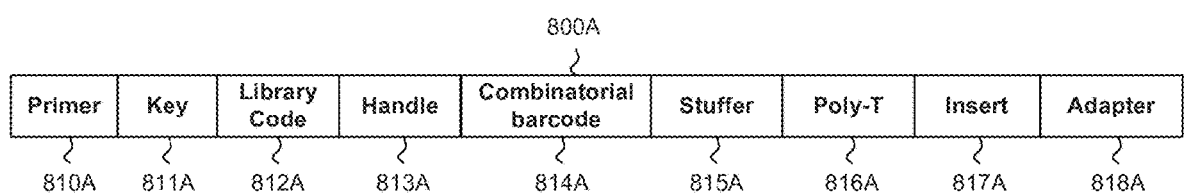
FIGS. 8A and 8B illustrate example read structures that incorporate combinatorial barcode sequences.

FIG. 8A schematically illustrates a read structure in accordance with various embodiments. For example, read structure 800A comprises a combinatorial barcode as described herein. The read structure 800A also includes a plurality of other nucleotide structures such that a library can be generated based on the sequencing output from the read. For example, read structure 800A begins with a primer sequence 810A that is used as a binding cite, for example for PCR amplification. The primer sequence 810A is followed by a key sequence 811A, for instance used for library identification. The key sequence 811A is followed by a library code 812A, which may comprise a barcode sequence used to identify a particular sample. The library code 812A is followed by a handle 813A, which can also comprise a binding cite for library construction, and may also be used to for phase synchronization purposes, as further described herein. The handle 813A is followed by a combinatorial barcode 814A, as described herein, that comprises a molecular barcode for identifying individual molecules (rather than a sample). The combinatorial barcode 814A is followed by a stuffer sequence 815A, for instance used for flow synchronization and/or phase correction over the read structure. The stuffer sequence 815A is followed by a poly-T section 816A, which can comprise a large number of T nucleotide bases. The poly-T section 816A is followed by the insert 817A, or sequence read targeted for sequencing. Finally, the insert 817A is followed by an adaptor 818A, such as an adaptor binding cite for binding the read structure to a fixed structure, such as a bead.

In an embodiment, read structure 800A may comprise a read structure for messenger RNA (mRNA) library construction. For example, read structure 800A may comprise a structure for a complementary DNA (cDNA) insert that corresponds to an mRNA target sequence. In this example, the poly-T section of the read sequence may comprise the complimentary portion of a poly-A tail of an mRNA target sequence. Poly-T sequencing can cause a number of potential errors without mitigation techniques. For example, a T to C transformation is a common PCR replication error (e.g., 0.3%). Where 60 T bases are included, a 0.3% error rate may cause up to 18% of reads to include a PCR error. T to C PCR errors split a long poly-T into multiple poly-T segments, separated by C's. In addition, a T homopolymer greater than a threshold level (e.g., 15 T's) can cause a large amount of incomplete extension due to only a finite number of T's being incorporated in any single nucleotide flow.

In some embodiments, a flow order for sequencing the poly-T section of the read structure can be determined to mitigate these potential sequencing errors. For example, an example flow order for the poly-T section may comprise T T T T C T T T C T T C T (SEQ. ID NO. 2). This flow order may mitigate a number of the potential errors described herein. Multiple T flows in a row mitigate the errors caused by only a finite number of T's incorporating in any single flow. For example, the first 5 T flows are used to soak up any pure T homopolymer sequences, thus mitigating against incomplete extension. The C flows then mitigate against any potential T to C PCR errors in the poly-T section. Lastly, the staggered C and T flows help incorporating poly-T segments after PCR errors and thus increase the probability of an in-phase sequencing for the insert following the Poly-T portion. An aggressively phase correcting flow order portion may be used directly after the poly-T flow order portion to mitigate any residual phasing effects stemming from the poly-T sequence that were not addressed by the poly-T flow order portion. An example of an aggressive flow order for mitigation against out of phase sequencing for the insert portion is T A C T A C G A C G T C G T A G T A C (SEQ. ID NO. 3), such that any remaining out of phase populations rejoin quickly and the number of low quality measurements for the insert is kept at a minimum.

The handle sequence and stuffer sequence can similarly be used to correct phase prior to sequencing the next part of the read, namely the combinatorial barcode sequence and poly-T section, respectively. For example, and example handle sequence, such as G T A G T A G T A C G (SEQ. ID NO. 4), can be used as a binding cite. A flow order based on the handle sequence can be designed to increase the time, or number of flows, used to sequence the handle, thus allowing slower reads to catch up to faster reads. For example, the flow order G G G T T A G G T A A A G T T T A C G (SEQ. ID NO. 5) includes a number of non-incorporating flows over the handle, thus enabling the phase advantages. Such a flow order for the handle may be useful to ensure the start of sequencing for the combinatorial barcode is in-phase for the reads.

In another example, an example stuffer sequence, such as A C G T A can also be used to provide phase benefits. A flow order based on the stuffer sequence can be designed to increase the time, or number of flows, used to sequence the stuffer, thus allowing slower reads to catch up to faster reads. For example, the flow order C G T A G T A C T A C G A C G T C G T (SEQ. ID NO. 6). A includes a number of non-incorporating flows over the stuffer, thus enabling the phase advantages. Such a flow order for the handle may be useful to ensure the start of sequencing for the poly-T section of the read is in-phase for the reads. In some embodiments, one or more poly-T section mitigation techniques may be implemented, as discussed herein. However, the effectiveness of these mitigation techniques may depend on an in-phase start for sequencing the poly-T. Accordingly, the phase correction capabilities of a stuffer and corresponding flow order may also benefit the poly-t sequencing.

As described herein, one or more flow orders may be implemented while sequencing a read structure, such as read structure 800A. For example, a sequence length for primer 810A, key 811A, library code 812A, handle 813A, combinatorial barcode 814A, and stuffer 815 A may be known (e.g., predetermined), and thus a flow order to sequence these portions of read structure 800A may be implemented. For example, primer flows may be used to sequence primer 810A, key flows may be used to sequence key 811A, library code flows may be used to sequence library key 812A, handle flows may be used to sequence handle 813A, combinatorial barcode flows may be used to sequence combinatorial barcode 814A, and/or stuffer flows may be used to sequence stuffer 815A. In some embodiments, a poly-T flow order, as described herein, may also be used to mitigate against sequencing errors over poly-T section 816A. Any suitable flow orders may be used to sequence insert 817A, such as a repeat of a predetermined order of nucleotide flows.

Figure 8B:
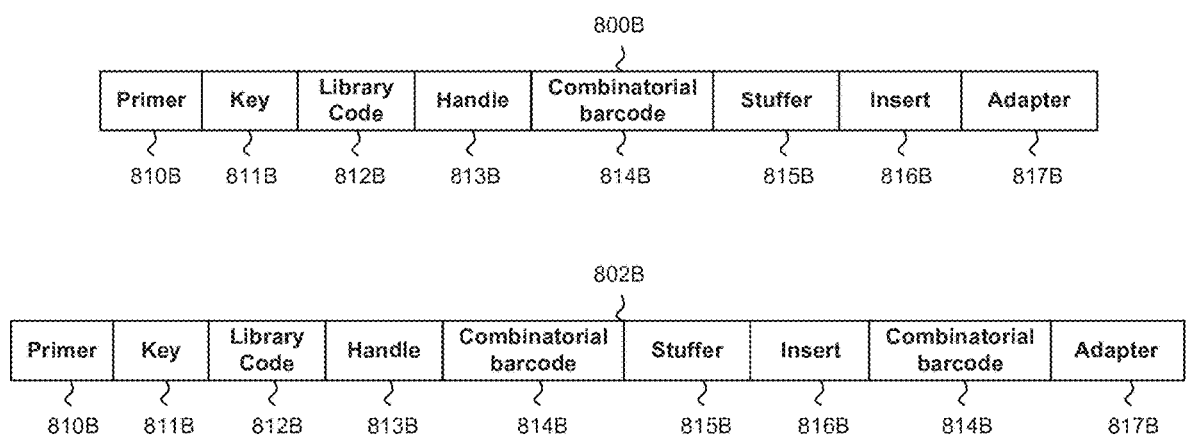

In various embodiments, the described combinatorial barcodes can be implemented for other read structures as well, for example read structures that do not correspond to mRNA target sequences and do not include a poly-T section. For example, FIG. 8B illustrates a read structure in accordance with various embodiments. Read structure 800B comprises a combinatorial barcode 814B as described herein. The read structure may include a plurality of other nucleotide structures such that a library may be generated based on the sequencing output from the read. For example, read structure 800B begins with a primer sequence 810B that is used as a binding cite, for example for PCR amplification. The primer sequence 810B is followed by a key sequence 811B, for instance used for library identification. The key sequence 811B is followed by a library code 812B, which may comprise a barcode sequence used to identify a particular sample. The library code 812B is followed by a handle 813B, which can also comprise a binding cite for library construction, and may also be used to for phase synchronization purposes, as further described herein. The handle 813B is followed by the combinatorial barcode 814B, as described herein, that comprises a molecular barcode for identifying individual molecules (rather than a sample). The combinatorial barcode 814B is followed by a stuffer sequence 815B, for instance used for flow synchronization over the read structure. The stuffer sequence 815B is followed by the insert 817B, or sequence read targeted for sequencing. Finally, the insert 817B may be followed by an adaptor 818B, such as an adaptor binding cite for binding the read structure to a fixed structure, such as a bead.

Figure 9A:
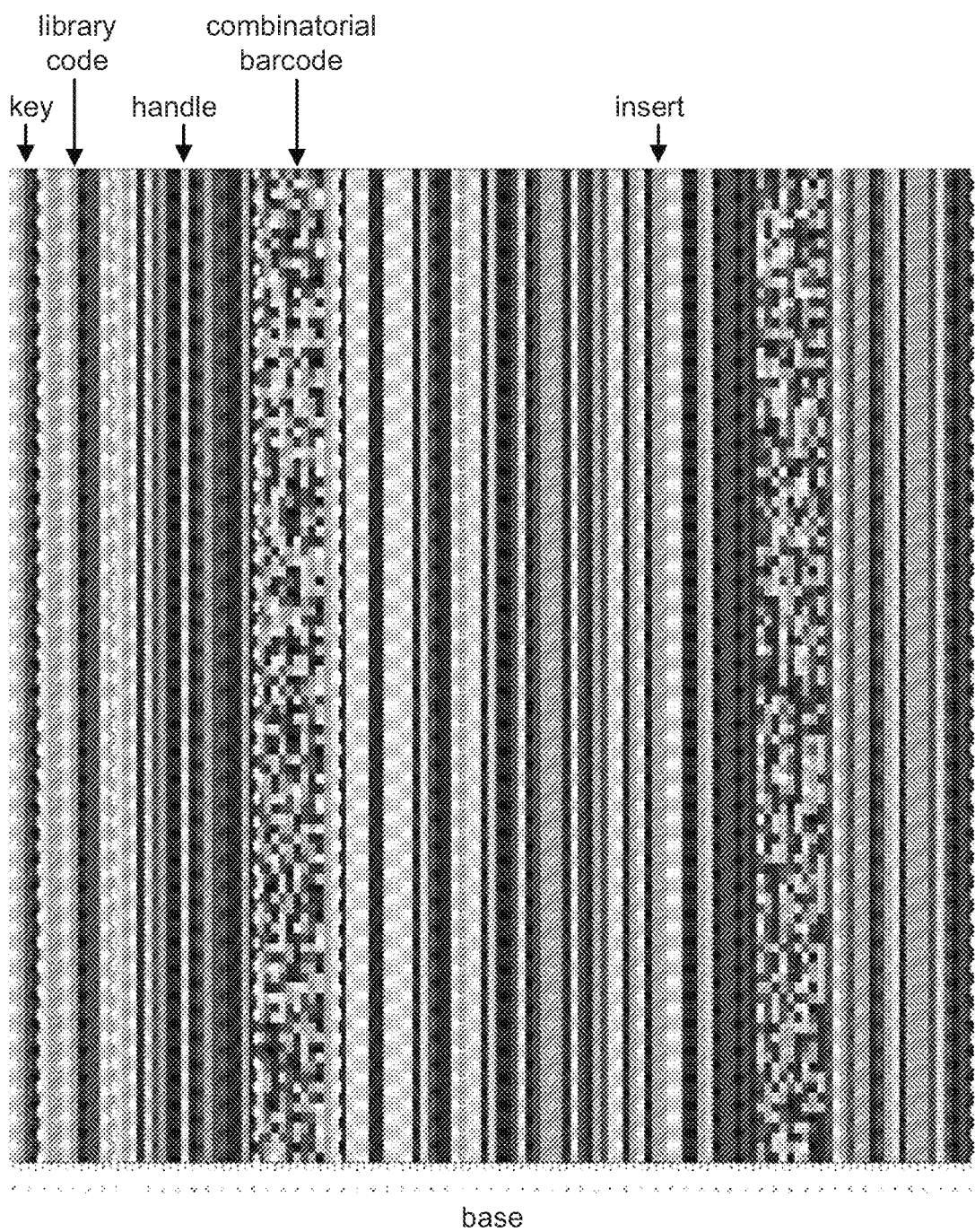
FIGS. 9A and 9B illustrate base space incorporation plots for sequence reads including combinatorial barcode sequences.

In some embodiments, a combinatorial barcode consistent with the disclosures herein may be implemented within read structure 800B. For example, a sequence motif of [H][V][K](n)[M][B][D](k) can be used to generate a plurality of combinatorial barcodes. As described herein, [H], [V], and [K] can represent groups of nucleotide bases for the potential combinations, and [M], [B], and [D] can be groups corresponding to the reverse complements of groups [H], [V], and [K], respectively. Although groups [M][B][D] can comprise the reverse complement of groups [H][V][K], for a given combinatorial barcode sequence the diversity bases in the [M][B][D] portion of the barcode are often not the reverse complement of the diversity bases of the [H][V][K] portion of the barcode. For instance, potential combinatorial barcode sequences according to a first iteration of the [H][V][K](n)[M][B][D](k) sequence motif can generate a number of potential barcode sequences where the [M][B][D] portion is not the reverse complement of the [H][V][K] portion. In an example, where n=3 and k=3, about 34 million combinatorial barcodes may be generated (18 possible combinations; 18^3=5.8K; 5.8K×5.8K=34 million). Given the potential ordering for bases, the sequence motif limits homopolymer length to no more than 2. In some embodiments, a modified flow order for sequencing over the combinatorial barcode is used that is determined based on the possible base combination for the sequence motif. The modified flow order may also be a repeated flow of 5 nucleotide bases that is repeated according to n and k, in this example 3+3=6 repetitions. FIG. 9A illustrates a base space incorporation plot for a sequence read that includes a combinatorial barcode sequence designed using the above-identified sequence motif. As described with reference to FIG. 8A, any number of different flow orders may be implemented for sequencing read structure 800B, such as predetermined flow orders for known sequence lengths of the read structure.

For example, a sequence length for primer 810B, key 811B, library code 812B, handle 813B, combinatorial barcode 814B, and stuffer 815B may be known (e.g., predetermined), and thus a flow order to sequence these portions of read structure 800A may be implemented. For example, primer flows may be used to sequence primer 810B, key flows may be used to sequence key 811B, library code flows may be used to sequence library key 812B, handle flows may be used to sequence handle 813B, combinatorial barcode flows may be used to sequence combinatorial barcode 814B, and/or stuffer flows may be used to sequence stuffer 815B. Any suitable flow orders may be used to sequence insert 817B, such as a repeat of a predetermined order of nucleotide flows.

As described, given an [H][V][K] sequence motif, barcodes generated from a combination of this motif would be expected to synchronize over the predetermined flow order [T C A C G][T]. Because [M][B][D] represents the reverse complement of [H][V][K], a reverse complement flow order for sequence motif [H][V][K] would be used to synchronize barcodes from sequence motif [M][B][D]. For example, barcodes generated from a combination of sequence motif [H][V][K](n)[M][B][D](k), would be expected to synchronize over a predetermined flow order that comprises repetitions of the flow order motif: [T C A C G](n)[T][A C G T G](k)[A]. In this example, the trailing [T] and [A] flows are used for synchronization. This flow order motif may be used to sequence combinatorial barcode 814B of read structure 800B.

Figure 9B:
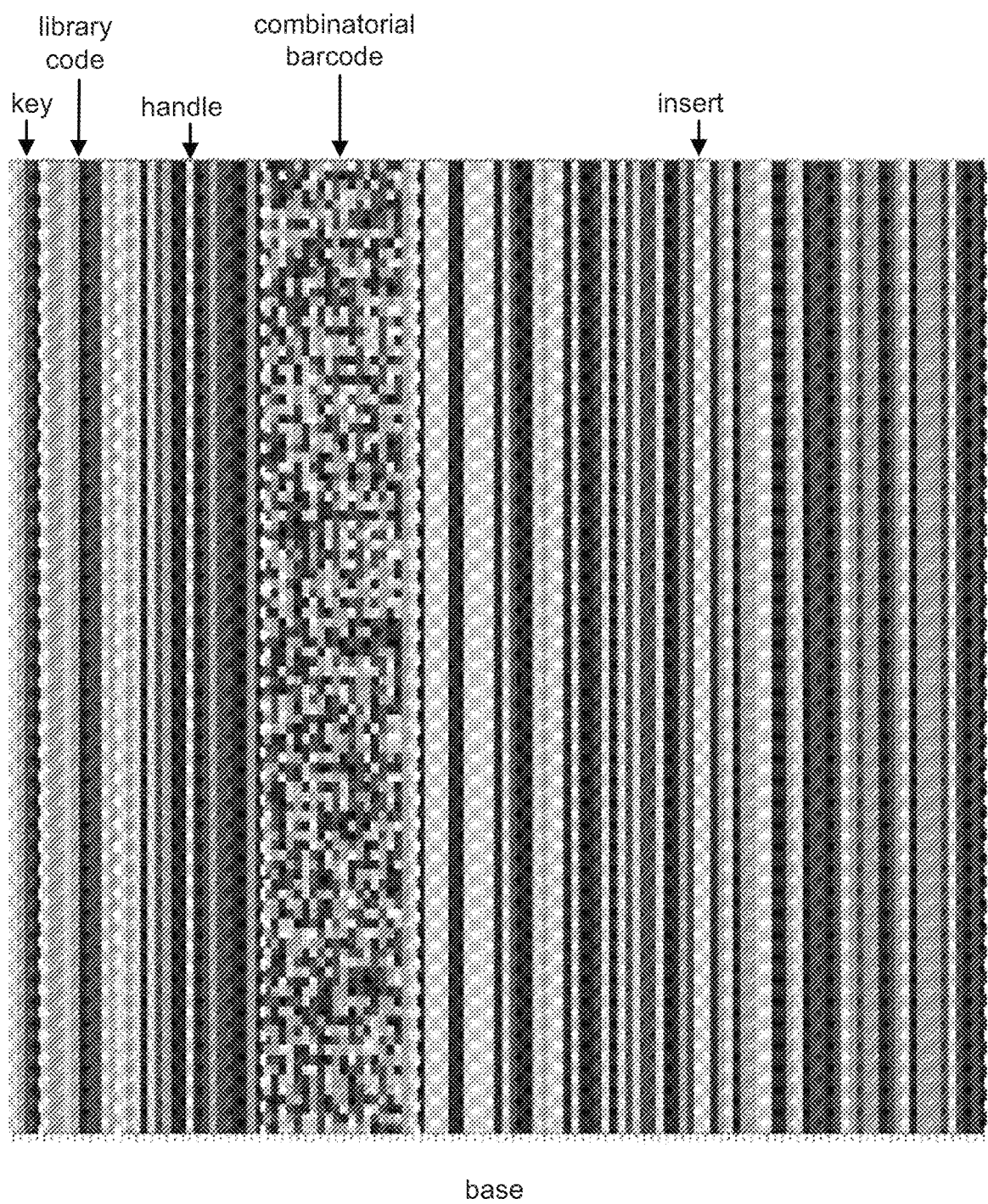

Read structure 802B, depicted in FIG. 8B, is similar to read structure 800B, except that the combinatorial barcode sequence 814B is placed before and after the insert 817, as illustrated. In some embodiments, combinatorial paired barcodes consistent with the disclosures herein may be implemented within read structure 800B. For example, a sequence motif of [H][V][K](n) paired with [M][B][D](k) may be used to generate a plurality of combinatorial barcodes. In this example, the [H][V][K](n) sequence motif may precede the insert while the [M][B][D] sequence motif follows the insert. In an example, where n=3 and k=3, about 34 million combinatorial barcodes may be generated (18 possible combinations; 18^3=5.8K; 5.8K×5.8K=34 million). Given the potential ordering for bases, the sequence motif limits homopolymer length to no more than 2. In some embodiments, a modified flow order for sequencing over the first combinatorial barcode (sequence motif [H][V][K](n)) can be used that is determined based on the possible base combinations for the sequence motif. The modified flow order may also be a repeated flow of 5 nucleotide bases that is repeated according to n, in this example 3 repetitions. Because of a variable insert size, flow synchronization is not achieved for the second combinatorial barcode (sequence motif [M][B][D](k)). FIG. 9B illustrates a base space incorporation plot for a sequence read that includes paired combinatorial barcode sequences designed using the above-identified sequence motif. As described with reference to FIG. 8A, any number of different flow orders may be implemented for sequencing read structure 802B, such as predetermined flow orders for known sequence lengths of the read structure. In various embodiments, the randomer-based tags described in U.S. patent application Ser. No. 15/178,450, filed Jun. 9, 2016 to Mongan et. al. may be replaced by one or more embodiments of the combinatorial barcode sequences described herein.

An exemplary experiment using combinatorial barcodes disclosed herein and randomer barcodes disclosed in U.S. patent application Ser. No. 15/178,450 generated experimental results in accordance with various embodiments. The experiment considered 3 sample barcode designs, [H][V][K](3)[M][B][D](3) (SEQ ID NO: 7), [H][V][K](3) paired with [M][B][D](3), and NNNACTNNNTGA (SEQ. ID NO. 8) (as disclosed with reference to U.S. patent application Ser. No. 15/178,450), for generating libraries. A set of 7 amplicons were used with 14 primers (F/R). When sequencing the combinatorial barcodes, the described combinatorial barcode flow order (the flow order motif according to the particular sequence motif) was flowed. For example, in a read structure similar to read structure 800B, a combinatorial barcode flow order may start after sequencing of handle 813B (e.g., given known sequence lengths for the barcode sequence prior to the combinatorial barcode). Provisional application 62/401,632 at appendices 1, 2, and 3, incorporated herein by reference, discloses sample primers, barcodes, and read structures in accordance with the experiment. The sequencing was performing using the Ion S5™ platform.

Libraries were generated for the seven amplicons using the randomer barcode sequences and the combinatorial barcode sequences. The experiment resulted in 10,737 average number of families for MegaMix libraries and 8,629 average number of families for cfDNA libraries generated by the randomer barcodes and 10,295 average number of families for MegaMix libraries and 7,712 average number of families for cfDNA libraries generated by the combinatorial barcodes. In addition, the randomer barcodes resulted in 18 true positives (TPs) and the combinatorial barcodes resulted in 16 TPs (avg) for MegaMix libraries. The randomer barcodes also resulted in 2 false positives (FPs) (avg) and 2 FPs (avg) for MegaMix libraries and cfDNA libraries, respectively, while the combinatorial barcodes resulted in 4 FPs (avg) and 1 FP for MegaMix libraries and cfDNA libraries, respectively.

In various embodiments, sample discriminating codes or barcodes can be designed based on one or more criteria set forth above (which may be taken alone or in combination). Various combinations of criteria can be chosen based on the sequencing experiment. Design criteria can include, but are not limited to, for example, the number of samples, the level of accuracy desired, the sensitivity of the sequencing instrument to detect individual samples, the accuracy of the sequencing instrument, and the like.

In various embodiments, sample discriminating codes or barcodes as set forth herein can be used in any suitable manner to assist in identifying or resolving samples. For example, barcodes can be used individually, or two or more barcodes can be used in combination. In an embodiment, a single barcode can identify one target sequence or multiple target sequences. For example, a single barcode can identify a group of target sequences. A barcode may be read separately from the target sequence or as part of a larger read operation spanning the barcode and a target sequence. The barcode may be positioned at any suitable position within the sample, including before or after a target sequence.

Figure 10:
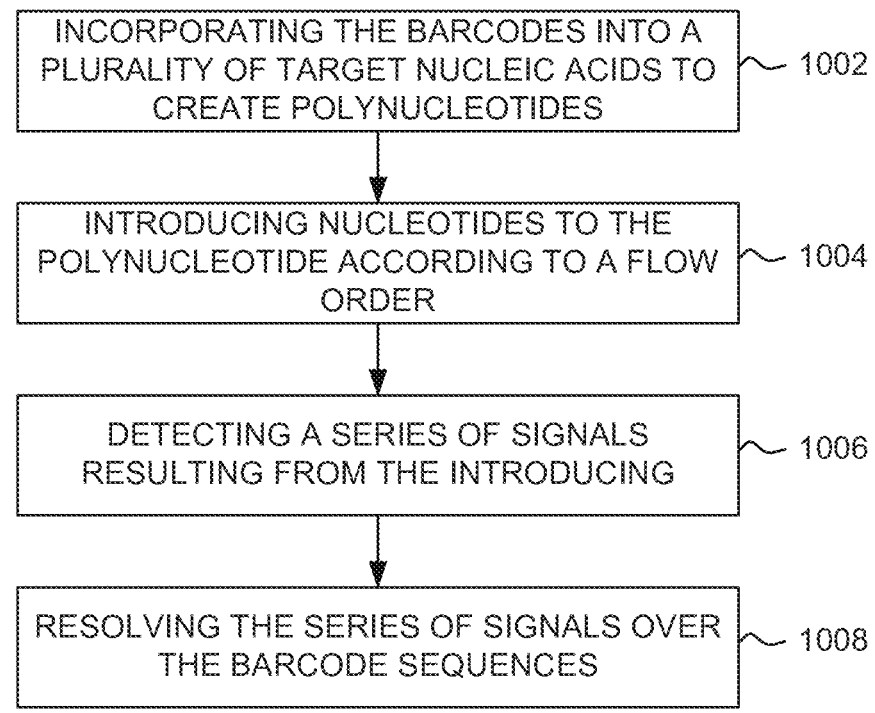
FIG. 10 illustrates exemplary parts of a workflow for sequencing polynucleotide samples with combinatorial barcode sequences.

FIG. 10 illustrates exemplary parts of a workflow for sequencing polynucleotide samples with combinatorial barcode sequences according to exemplary embodiments of the present disclosure. For example, plurality of combinatorial barcode sequences may be sequence according to one or more predetermined flow orders in accordance with exemplary embodiments described herein.

At step 1002, the plurality of combinatorial barcodes are incorporated into a plurality of target nucleic acids to create tagged polynucleotides. For example, the barcodes may be attached to the target nucleic acids as described herein or by any conventional means such that signals obtained over the barcodes during sequencing may identify the particular target nucleic acid attached to the barcode. In an embodiment, the combinatorial barcode sequences comprise at least two iterations of a sequence motif, wherein the sequence motif comprises a first nucleotide base from a first group of nucleotide bases followed by a second nucleotide base from a second group of nucleotide bases, the first group and the second group differing from each other. For example, the sequence motif may be any of the sequence motifs described in this disclosure.

At step 1004, a series of nucleotides are introduced to the polynucleotides according to one or more predetermined flow orders. For example, reactions to the tagged polynucleotides may be caused by introducing sequential nucleotide flows comprising one species of nucleotide, the flows being in a predetermined order based on the nucleotide species. The reacting may comprise incorporations of nucleotides from the nucleotide flows into the tagged polynucleotides over the barcode sequences.

At step 1006, a series of signals resulting from the incorporations is detected. For example, hydrogen ions released by the incorporation of nucleotides into the polynucleotides may be detected, wherein the amplitude of the signals is related to the amount of hydrogen ions detected. In another example, inorganic pyrophosphate released by the incorporation of nucleotides into the polynucleotide may be detected, wherein the amplitude of the signals is related to the amount of inorganic pyrophosphate detected. In some embodiments, the predetermined order of nucleotide flows may comprise a repetition of a flow order motif that is based on the sequence motif, as described in this disclosure. At step 1008, a series of signals over the barcode sequences is resolved to determine the barcode sequences. For example, one or more of the barcode sequences may be used to identify the target sequences.

Manufacturing of Barcodes

In various embodiments, the barcode manufacturing comprises manufacturing of the forward barcode, forward primer (P1a), reverse barcode, and reverse primer (P1b). In an embodiment, in an initial step these oligonucleotides may be purified, where all of the oligonucleotides are normalized to 100-400 µM in a TE or low TE buffer. In an embodiment, the oligonucleotides that are non-ligating (e.g., the reverse barcode and P1b) may be purified using High Performance Liquid Chromatography (HPLC) while the oligonucleotides that are ligating (e.g., the forward barcode and P1a) may be purified using a desalting technique. Those having ordinary skill in the art are familiar with various desalting techniques that can be used in barcode manufacturing.

For example, use of HPLC for the reverse barcode and P1b may help mitigate against sequencing error. Oligonucleotides are synthesized from 3' to 5', and thus failed syntheses from reverse barcode and P1b are potentially truncated at the 5' end. A lack of HPLC treatment for these strands may increase adapter dimer (e.g., from substantially 0% to substantially 5-15%). In addition, if the forward barcode and P1a are directly ligated to the amplicon, any cross-contamination may lead to base miscalling. In addition, with a large number of sequences, HPLC may be both cost-prohibitive (or otherwise cost inefficient) and prone to cross-contamination. Desalting these strands rather than performing HPLC is less expensive and does not require the strands to be used on common lab equipment (i.e., HPLC instrument) thus eliminating a source of cross contamination. Further, during nick translation, the reverse barcode and P1b are overwritten by DNA polymerase using the forward barcode and P1a as a template, thus removing any contamination originating from HPLC contamination of P1b and reverse barcode sequences. This can further reduce contamination risk for the strands on which HPLC is performed.

In an embodiment, after purification, equal volumes of forward and reverse barcode oligonucleotides and P1a and P1b oligonucleotides can be combined and annealed in separate tubes using certain annealing conditions. For example, the annealing conditions can comprise: denaturing at 95° C. for 5 minutes; performing 64 cycles starting at 89° C. for 2 minutes with a 1° C. decrease every 2 minutes; and holding at 4° C. for 1 hour and up to overnight (e.g., between 6 and 12 hours).

After annealing, equal volumes of annealed barcode adaptor and P1 adaptor can be combined. The sample can be diluted 5-fold with a low TE buffer. And 2 µL of diluted mixture/AmpliSeq reaction may be added. Other variations of barcode manufacturing may similarly be implemented. In an embodiment, the step of manufacturing the barcodes may comprise synthesizing the polynucleotide. A polynucleotide containing the barcode sequence may be made using any conventional polynucleotide synthesis technique known in the art.

In some embodiments, for instance with respect to application to mRNA, oligonucleotides may be incorporated by priming, for instance using oligo-dT (a sequence of deoxythymidine nucleotides), and which can be extended using reverse transcription to create a strand. A second strand can be generated using any suitable technique, such as random priming. In some embodiments, annealing, such as the annealing described above, is not performed for mRNA applications.

According to various exemplary embodiments, the manufactured barcodes are combined to form a kit of barcodes for use for sequencing. The sequencing kit can further comprise a polymerase enzyme and multiple containers for holding the different polynucleotides, with each different polynucleotide may be held in a different container. The polynucleotides can be oligonucleotides of 5-40 bases in length. The sequencing kit can further comprise multiple different kinds of nucleotide monomers. The sequencing kit may further comprise a ligase enzyme.

In some embodiments, a sequencing kit comprises multiple different polynucleotides (which may be contained in vials or other containers, for example), each different polynucleotide comprising a different barcode sequence as described herein. The polynucleotides may be oligonucleotides having 5-40 bases. The polynucleotides may be the barcode sequences themselves, or they may further include other elements, such as primer sites, adaptors, ligating sites, linkers, etc. The sequencing kit also can include a set of precursor nucleotide monomers for carrying out sequencing-by-synthesis operations, for example, and/or various other reagents involved in a workflow for preparing and/or sequencing a sample.

In some embodiments, the scale of multiplexing that is enabled by the large number of provided barcodes facilitates certain sequencing applications. For example, genotyping by sequencing, clone verification, and other test synthesis verification (e.g., to verify a synthesized sequence is correct) can be performed more efficiently with a large number of barcodes that enable a high degree of multiplexing. In some embodiments, the present disclosure contemplates a non-transitory machine-readable storage medium comprising instructions which, when executed by a processor, cause the processor to perform such methods and variants thereof as detailed herein. A system according to an exemplary embodiment of the present disclosure includes a machine-readable memory; and a processor configured to execute machine-readable instructions, which, when executed by the processor, cause the system to perform such methods and variants thereof as detailed herein.

Figure 11A:
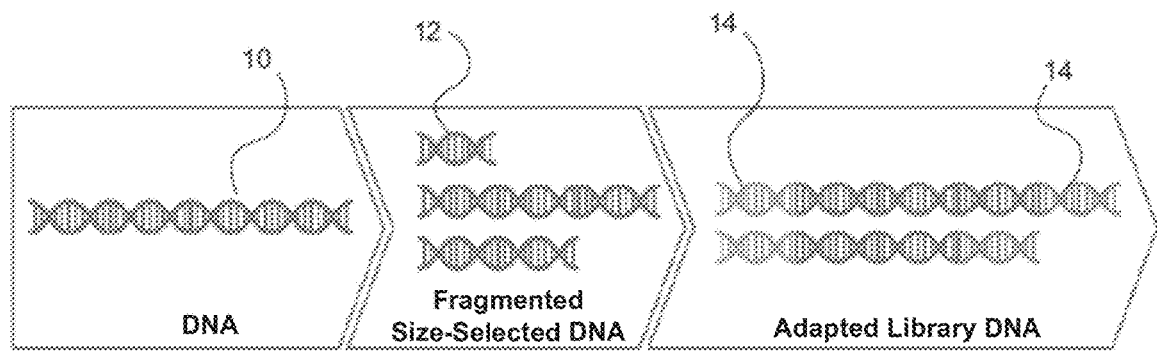
FIGS. 11A-11C schematically illustrate an exemplary workflow for preparing a multiplex sample.
Figure 11B:
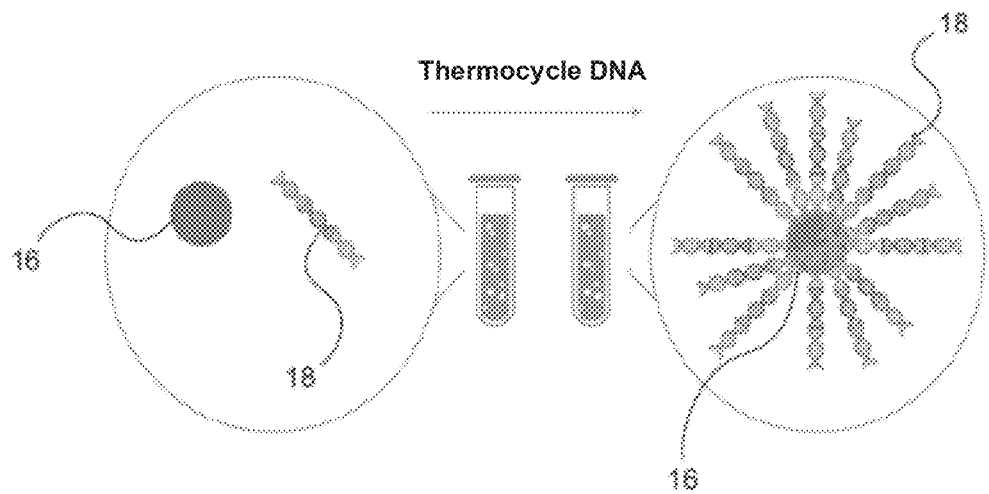
Figure 11C:
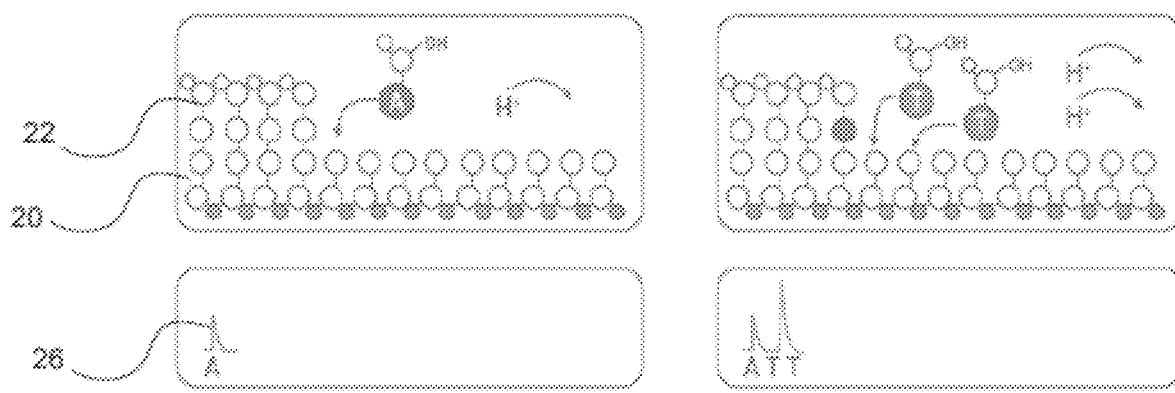

FIGS. 11A-11C illustrate an exemplary workflow for preparing a multiplex sample. FIG. 11A shows an exemplary construction of a genomic DNA fragment library. A bacterial genomic DNA 10 can be fragmented into many DNA fragments 12 using any suitable technique, such as sonication, mechanical shearing, or enzymatic digestion, for example. Platform-specific adaptors 14 are then be ligated onto the ends of the fragments 12. Referring to FIG. 11B, each fragment sample 18 is then be isolated and combined with a bead 16. To allow for identification of the fragment 18, a barcode sequence (not shown in the figure) can be ligated to the fragment 18. The fragment 18 is then clonally amplified onto the bead 16, resulting in many clonal copies of the fragment 18 on the bead 16. This process may repeated for each different fragment 12 of the library, resulting in many beads, each having the product of a single library fragment 12 amplified many times. Referring to FIG. 11C, the beads 16 are then loaded onto a reaction chamber array (e.g., microwell array). FIG. 11C shows a partial view of a DNA fragment inside a reaction chamber as it is undergoing sequencing reactions. A template strand 20 is be paired with a growing complementary strand 22. In the left panel, an A nucleotide is added to the reaction chamber (or flowed), resulting in a single-base incorporation event, which generates a single hydrogen ion. In the right panel, a T nucleotide is added to the reaction chamber, resulting in a two-base incorporation event, which generates two hydrogen ions.

In various embodiments, a sequencing kit contains one or more of the materials needed for the above sample preparation and sequencing workflow, including reagents for performing DNA fragmentation, adaptors, primers, ligase enzymes, beads or other solid support, polymerase enzymes, or precursor nucleotide monomers for the incorporation reactions.

According to an exemplary embodiment, the present disclosure contemplates a system comprising a plurality of identifiable nucleic acid barcodes. The nucleic acid barcodes may be attached to, or associated with, target nucleic acid fragments to form barcoded target fragments (e.g., polynucleotides). A library of barcoded target fragments may include a plurality of a first barcode attached to target fragments from a first source. Alternatively, a library of barcoded target fragments may include different identifiable barcodes attached to target fragments from different sources to make a multiplex library. For example, a multiplex library may include a mixture of a plurality of a first barcode attached to target fragments from a first source, and a plurality of a second barcode attached to target fragments from a second source. In the multiplex library, the first and second barcodes may be used to identify the source of the first and second target fragments, respectively. Any number of different barcodes can be attached to target fragments from any number of different sources. In a library of barcoded target fragments, the barcode portion is used to identify: a single target fragment; a single source of the target fragments; a group of target fragments; target fragments from a single source; target fragments from different sources; target fragments from a user-defined group; and/or any other grouping that may require or benefit from identification. The sequence of the barcoded portion of a barcoded target fragment may be separately read from the target fragment, or read as part of a larger read spanning the barcode and the target fragment. In a sequencing experiment, the nucleic acid barcode may be sequenced with the target fragment and then parsed algorithmically during processing of the sequencing data. In various embodiments, a nucleic acid barcode may comprise a synthetic or natural nucleic acid sequence, DNA, RNA, or other nucleic acids and/or derivatives. For example, a nucleic acid barcode may include nucleotide bases adenine, guanine, cytosine, thymine, uracil, inosine, or analogs thereof. Such barcodes may serve to identify a polynucleotide strand and/or distinguish it from other polynucleotide strands (e.g., those containing a different target sequence of interest), and may be used for various purposes, such as tracking, sorting, and/or identifying the samples, for example. Because different barcodes can be associated with different polynucleotide strands, such barcodes may be useful in multiplexed sequencing of different samples.

Multiplex Libraries

In various embodiments, the present disclosure contemplates sample discriminating codes or barcodes (e.g., nucleic acid barcodes) that are attached to, or associated with, targets (e.g., nucleic acid fragments) to generate barcoded libraries (e.g., barcoded nucleic acid libraries). Such libraries can be prepared using one or more suitable nucleic acid or biomolecule manipulation procedures, including, but not limited to: fragmenting; size-selecting; end-repairing; tailing; adaptor-joining; nick translation; and purification, for example. In various embodiments, nucleic acid barcodes can be attached to, or associated with, fragments of a target nucleic acid sample using one or more suitable procedure, including, but not limited to, ligation, cohesive-end hybridization, nick-translation, primer extension, or amplification, for example. In some embodiments, nucleic acid barcodes may be attached to a target nucleic acid using amplification primers having a particular barcode sequence.

In various embodiments, a target nucleic acid or biomolecule (e.g., proteins, polysaccharides, and nucleic acids, and their polymer subunits, etc.) sample may be isolated from any suitable source, such as solid tissue, tissue, cells, yeast, bacteria, or similar sources, for example. Any suitable methods for isolating samples from such sources may be used. For example, solid tissue or tissue may be weighed, cut, mashed, homogenized, and the sample may be isolated from homogenized samples. An isolated nucleic acid sample may be chromatin, which may be cross-linked with proteins that bind DNA, in a procedure known as ChIP (chromatin immunoprecipitation). In some embodiments, samples may be fragmented using any suitable procedure, including cleaving with an enzyme or chemical, or by shearing. Enzyme cleavage may include any type of restriction endonuclease, endonuclease, or transposase-mediated cleavage.

In some embodiments, libraries and/or beaded templates may be implemented with the disclosed barcodes. For example, U.S. patent application Ser. No. 13/599,876, published Feb. 28, 2015 as U.S. Patent Pub. No. 2013/0053256, to Hubbell, entitled METHODS, SYSTEMS, AND KITS FOR SAMPLE IDENTIFICATION, which is incorporated herein by reference in its entirety, further discloses Mate Pair Libraries, Paired End Libraries, SAGE™ libraries, Yeast libraries, and ChIP-Seq libraries that may be implemented with various disclosed embodiments.

According to various embodiments, one or more features of any one or more of the above-discussed teachings and/or embodiments may be performed or implemented using appropriately configured and/or programmed hardware and/or software elements. Determining whether an embodiment is implemented using hardware and/or software elements may be based on any number of factors, such as desired computational rate, power levels, heat tolerances, processing cycle budget, input data rates, output data rates, memory resources, data bus speeds, etc., and other design or performance constraints.

Examples of hardware elements may include processors, microprocessors, input(s) and/or output(s) (I/O) device(s) (or peripherals) that are communicatively coupled via a local interface circuit, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory. The processor can be any custom made or commercially available processor, a central processing unit (CPU), an auxiliary processor among several processors associated with the computer, a semiconductor based microprocessor (e.g., in the form of a microchip or chip set), a macroprocessor, or generally any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem; for accessing another device, system, or network), a radio frequency (RF) or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system (O/S), which may control the execution of other computer programs such as the system, and provides scheduling, input-output control, file and data management, memory management, communication control, etc.

According to various embodiments, one or more features of any one or more of the above-discussed teachings and/or embodiments may be performed or implemented using appropriately configured and/or programmed non-transitory machine-readable medium or article that may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, etc., including any medium suitable for use in a computer. Memory can include any one or a combination of volatile memory elements (e.g., random access memory (RAM, such as DRAM, SRAM, SDRAM, etc.)) and nonvolatile memory elements (e.g., ROM, EPROM, EEROM, Flash memory, hard drive, tape, CDROM, etc.). Moreover, memory can incorporate electronic, magnetic, optical, and/or other types of storage media. Memory can have a distributed architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

According to various embodiments, one or more features of any one or more of the above-discussed teachings and/or embodiments may be performed or implemented at least partly using a distributed, clustered, remote, or cloud computing resource.

According to various embodiments, one or more features of any one or more of the above-discussed teachings and/or embodiments may be performed or implemented using a source program, executable program (object code), script, or any other entity comprising a set of instructions to be performed. When a source program, the program can be translated via a compiler, assembler, interpreter, etc., which may or may not be included within the memory, so as to operate properly in connection with the O/S. The instructions may be written using (a) an object oriented programming language, which has classes of data and methods, or (b) a procedural programming language, which has routines, subroutines, and/or functions, which may include, for example, C, C++, Pascal, Basic, Fortran, Cobol, Perl, Java, and Ada.

According to various embodiments, one or more of the above-discussed embodiments may include transmitting, displaying, storing, printing or outputting to a user interface device, a computer readable storage medium, a local computer system or a remote computer system, information related to any information, signal, data, and/or intermediate or final results that may have been generated, accessed, or used by such embodiments. Such transmitted, displayed, stored, printed or outputted information can take the form of searchable and/or filterable lists of runs and reports, pictures, tables, charts, graphs, spreadsheets, correlations, sequences, and combinations thereof, for example.

Various other embodiments may be derived by repeating, adding, or substituting any generically or specifically described features and/or components and/or substances and/or steps and/or operating conditions set forth in one or more of the above-described embodiments. Further, it should be understood that an order of steps or order for performing certain actions is immaterial so long as the objective of the steps or action remains achievable, unless specifically stated otherwise. Furthermore, two or more steps or actions can be conducted simultaneously so long as the objective of the steps or action remains achievable, unless specifically stated otherwise. Moreover, any one or more feature, component, aspect, step, or other characteristic mentioned in one of the above-discussed embodiments may be considered to be a potential optional feature, component, aspect, step, or other characteristic of any other of the above-discussed embodiments so long as the objective of such any other of the above-discussed embodiments remains achievable, unless specifically stated otherwise.

Although various embodiments of the present teachings may advantageously be used with sequencing-by-synthesis approaches, as described herein and in Rothberg et al., U.S. Pat. Publ. No. 2009/0026082; Anderson et al., SENSORS AND ACTUATORS B CHEM., 129:79-86 (2008); Pourmand et al., PROC. NAT1. ACAD. SCI., 103:6466-6470 (2006), which are all incorporated by reference herein in their entirety, for example, the present teachings may also be used with other approaches, such as variants of sequencing-by-synthesis including methods where the nucleotides or nucleoside triphosphate precursors are modified to be reversible terminators (sometimes referred to as cyclic reversible termination (CRT) methods) and methods where the nucleotides or nucleoside triphosphate precursors are unmodified (sometimes referred to as cyclic single base delivery (CSD) methods), for example, or more generally methods that comprise repeated steps of delivering (or extending in response to delivering) nucleotides (to the polymerase-primer-template complex) and collecting signals (or detecting the incorporation either directly or indirectly).

Although various embodiments of the present teachings may advantageously be used in connection with pH-based sequence detection, as described herein and in Rothberg et al., U.S. Pat. Appl. Publ. Nos. 2009/0127589 and 2009/0026082 and Rothberg et al., U.K. Pat. Appl. Publ. No. GB2461127, which are all incorporated by reference herein in their entirety, for example, the present teachings may also be used with other detection approaches, including the detection of pyrophosphate (PPi) released by the incorporation reaction (see, e.g., U.S. Pat. Nos. 6,210,891; 6,258,568; and 6,828,100); various fluorescence-based sequencing instrumentation (see, e.g., U.S. Pat. Nos. 7,211,390; 7,244,559; and 7,264,929); some sequencing-by-synthesis techniques that can detect labels associated with the nucleotides, such as mass tags, fluorescent, and/or chemiluminescent labels (in which case an inactivation step may be included in the workflow (e.g., by chemical cleavage or photobleaching) prior to the next cycle of synthesis and detection)); and more generally methods where an incorporation reaction generates or results in a product or constituent with a property capable of being monitored and used to detect the incorporation event, including, for example, changes in magnitude (e.g., heat) or concentration (e.g., pyrophosphate and/or hydrogen ions), and signal (e.g., fluorescence, chemiluminescence, light generation), in which cases the amount of the detected product or constituent may be monotonically related to the number of incorporation events, for example.

Although the present description describes in detail various exemplary embodiments, other embodiments are also possible and within the scope of the present invention. For example, those skilled in the art may appreciate from the present description that the present teachings may be implemented in a variety of forms, for example, using various sequencing instruments, and that the various embodiments may be implemented alone or in combination. Variations and modifications will be apparent to those skilled in the art from consideration of the specification and figures and practice of the teachings described in the specification and figures, and the claims.

The invention claimed is:

1. A method for nucleic acid sequencing, the method comprising:
   incorporating into a polynucleotide a combinatorial barcode sequence to create a tagged polynucleotide, the combinatorial barcode sequence comprising at least two iterations of a sequence motif, the sequence motif comprising a first nucleotide base from a first group of nucleotide bases, followed by a second nucleotide base from a second group of nucleotide bases, followed by a third nucleotide base from a third group of nucleotide bases, wherein:
   the first group, the second group, and the third group differ from each other,
   two groups of the first, second, and third groups contain at least two different nucleotide bases, and
   at least one of the first, second, and third groups comprises at least three different nucleotide bases;
   causing reactions with the tagged polynucleotide by introducing sequential nucleotide flows comprising one species of nucleotide, the flows being in a predetermined order based on the nucleotide species, wherein the reactions comprise incorporations of nucleotides from the nucleotide flows into the tagged polynucleotide over the barcode sequence;
   detecting a series of signals over the barcode sequence resulting from the incorporations, wherein the predetermined order of nucleotide flows comprises a repetition of a flow order motif that is based on the sequence motif; and
   resolving the detected series of signals to determine the combinatorial barcode sequence,
   wherein the combinatorial barcode sequence is one of at least eight potential combinatorial barcode sequences, and the potential combinatorial barcode sequences are synchronized in flow space based on the predetermined order of nucleotide flows.

2. The method of claim 1, wherein the predetermined order of nucleotide flows comprises a modified portion of a first flow order for sequencing the tagged polynucleotide.

3. The method of claim 1, wherein the first group comprises at least three different nucleotide bases and the second group comprises at least three different nucleotide bases.

4. The method of claim 1, wherein the sequence motif further comprises, following the third nucleotide base, a fourth nucleotide base from a fourth group of nucleotide bases, the fourth group comprising at least two different nucleotide bases, and each of the first, second, third, and fourth groups differing from each other.

5. The method of claim 4, wherein the sequence motif comprises at least 36 possible combinations of nucleotide bases.

6. The method of claim 5, wherein a length of the combinatorial barcode sequence is 20 nucleotide bases that correspond to 5 iterations of the sequence motif or 24 nucleotide bases that correspond to 6 iterations of the sequence motif.

7. The method of claim 6, wherein the combinatorial barcode is one of over 1,000,000 potential combinatorial barcode sequences based on 5 iterations of the sequence motif.

8. The method of claim 1, wherein the first group comprises at least three different nucleotide bases, the second group comprises at least three different nucleotide bases, and the third group comprises at least three different nucleotide bases.

9. The method of claim 1, wherein the sequence motif comprises 18 possible combinations of nucleotide bases.

10. The method of claim 9, wherein a length for the combinatorial barcode sequence is 15 nucleotide bases that correspond to 5 iterations of the sequence motif or 18 nucleotide bases that correspond to 6 iterations of the sequence motif.

11. The method of claim 10, wherein the combinatorial barcode is one of over 1,000,000 potential combinatorial barcode sequences based on 5 iterations of the sequence motif.

12. The method of claim 1, wherein the combinatorial barcodes sequence has a length comprising a length for the sequence motif multiplied by the number of iterations for the sequence motif.

13. The method of claim 1, wherein the combinatorial barcode sequence is one of over 1,000,000 potential combinatorial barcode sequences.

14. The method of claim 1, wherein the first group comprises T, A, and C as nucleotide bases, the second group comprises A, C, and G as nucleotide bases, and the third group comprises G and T as nucleotide bases.

15. The method of claim 14, wherein there are at least five iterations of the sequence motif.

16. The method of claim 14, wherein:
the sequence motif is a first sequence motif, and
the combinatorial barcode further comprises a second sequence motif following the first sequence motif, the second sequence motif comprising a fourth nucleotide base from a fourth group of nucleotide bases, followed by a fifth nucleotide base from a fifth group of nucleotide bases, and followed by a sixth nucleotide based from a sixth group of nucleotide bases,
wherein the fourth, fifth, and sixth groups differ from each other, and each of the fourth, fifth, and sixth groups contain at least two different nucleotide bases.

17. The method of claim 16, wherein the fourth group comprises A, T, and G as nucleotide bases, the second group comprises T, G, and C as nucleotide bases, and the third group comprises C and A as nucleotide bases.

18. The method of claim 16, wherein the combinatorial barcode comprises the same number of iterations of the second sequence motif as the first sequence motif.

19. The method of claim 1, wherein the first group comprises A, T, and G as nucleotide bases, the second group comprises T, G, and C as nucleotide bases, and the third group comprises C and A as nucleotide bases.

20. The method of claim 19, wherein:
the sequence motif is a first sequence motif;
the combinatorial barcode further comprises a second sequence motif following the first sequence motif, the second sequence motif comprising a fourth nucleotide base from a fourth group of nucleotide bases, followed by a fifth nucleotide base from a fifth group of nucleotide bases, and followed by a sixth nucleotide based from a sixth group of nucleotide bases, the fourth, fifth, and sixth groups differing from each other, each of the fourth, fifth, and sixth groups containing at least two different nucleotide bases;
wherein:
the fourth group comprises T, A, and C as nucleotide bases, the second group comprises A, C, and G as nucleotide bases, and the third group comprises G and T as nucleotide bases; and
the combinatorial barcode comprises the same number of iterations of the second sequence motif as the first sequence motif.

* * * * *